United States Patent
Goutsis et al.

(10) Patent No.: US 9,504,639 B2
(45) Date of Patent: Nov. 29, 2016

(54) COMPOSITION FOR TREATING KERATINOUS FIBRES, COMPRISING SPECIFIC AMINOSILICONES, ACIDS AND DIRECT DYES

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/645,619

(22) Filed: Mar. 12, 2015

(65) Prior Publication Data
US 2015/0182441 A1    Jul. 2, 2015

Related U.S. Application Data

(63) Continuation of application No. PCT/EP2013/068973, filed on Sep. 13, 2013.

(30) Foreign Application Priority Data

Sep. 18, 2012   (DE) ................ 10 2012 216 606

(51) Int. Cl.
| | |
|---|---|
| *A61Q 5/00* | (2006.01) |
| *A61K 8/898* | (2006.01) |
| *A61K 8/362* | (2006.01) |
| *A61K 8/365* | (2006.01) |
| *A61K 8/368* | (2006.01) |
| *A61K 8/55* | (2006.01) |
| *A61Q 5/06* | (2006.01) |
| *A61Q 5/10* | (2006.01) |

(52) U.S. Cl.
CPC ............ *A61K 8/898* (2013.01); *A61K 8/362* (2013.01); *A61K 8/365* (2013.01); *A61K 8/368* (2013.01); *A61K 8/55* (2013.01); *A61Q 5/065* (2013.01); *A61Q 5/10* (2013.01); *A61K 2800/4324* (2013.01)

(58) Field of Classification Search
CPC ...... A61Q 5/065; A61K 8/898; A61K 8/365; A61K 8/36; A61K 8/362; A61K 8/432
USPC .............................................. 8/449
See application file for complete search history.

(56) References Cited

U.S. PATENT DOCUMENTS

| | | |
|---|---|---|
| 4,820,308 A | 4/1989 | Madrange et al. |
| 2003/0147841 A1 | 8/2003 | Legrand et al. |
| 2005/0015896 A1* | 1/2005 | Pratt ............... A61K 8/40 8/405 |
| 2005/0095214 A1* | 5/2005 | Ohta ............... A61K 8/39 424/70.12 |
| 2005/0255075 A1 | 11/2005 | Meder et al. |
| 2009/0074699 A1 | 3/2009 | Biganska et al. |
| 2013/0310295 A1 | 11/2013 | Iwai |

FOREIGN PATENT DOCUMENTS

| | | |
|---|---|---|
| DE | 19757508 A1 | 6/1999 |
| DE | 102011089686 A1 | 8/2012 |
| WO | 97/38667 A1 | 10/1997 |
| WO | WO 2012/079915 A2 * | 6/2012 ............... A61Q 5/04 |

OTHER PUBLICATIONS

STIC Search Report dated Apr. 29, 2015.*
PCT International Search Report (PCT/EP2013/068973) dated Jul. 8, 2014.
Reich et al., "Light Scattering and Shine Measurements of Human Hair: A Sensitive Probe of the Hair Surface", Journal of the Society of Cosmetic Chemists, vol. 44, pp. 221-234, 1993.

* cited by examiner

*Primary Examiner* — Eisa Elhilo
(74) *Attorney, Agent, or Firm* — P. Scott Smith

(57) ABSTRACT

Composition for treating keratinous fibers, more particularly human hair, comprising in a cosmetically appropriate vehicle a) at least one organic and/or inorganic acid, b) at least one direct dye and c) at least one compound of the formula (I).

18 Claims, No Drawings

COMPOSITION FOR TREATING KERATINOUS FIBRES, COMPRISING SPECIFIC AMINOSILICONES, ACIDS AND DIRECT DYES

FIELD OF THE INVENTION

The present invention generally relates to agents for treating keratinic fibers, in particular human hair, which contain at least one specific aminosilicone, at least one inorganic and/or organic acid, and at least one direct dye. The present patent application further relates to the use of this particular composition for creating a long-lasting luster on the hair, and a corresponding method.

BACKGROUND OF THE INVENTION

The care and treatment of human hair represents an important part of daily hygiene. In addition, changing the color of the hair is a key area of modern cosmetics. Shampoos and conditioners are among the hair treatment products customarily applied several times a week, often even daily. Changing the color of the hair generally takes place at longer intervals, but is likewise of importance to the consumer with regard to personal appearance, since it represents a fashionable form of expression as well as an option for concealing gray hair.

Hair treatment products which impart a high luster are particularly desirable for the consumer. Lustrous hair looks attractive and healthy, and the hairstyle is perceived as being well cared for and full of vitality. Within the scope of development work on cosmetic agents which produce lustrous hair, numerous efforts have already been undertaken, and a correspondingly large number of products is on the market.

Despite this extensive development work, it has not been possible thus far to find formulations by means of which a long-lasting luster may be produced.

Heretofore, although the hair exhibited a satisfactory luster directly after applying such formulations, the luster faded after washing the hair, at the latest after a few repeated washings of the hair, since the active substances which produced the luster were also rinsed out during washing. Accordingly, a long-lasting luster that is resistant to multiple hair washings is not achievable using the agents of the prior art.

BRIEF SUMMARY OF THE INVENTION

Agent for treating keratinic fibers, in particular human hair, which contains in a cosmetically suitable carrier, at least one inorganic and/or organic acid; at least one direct dye; and at least one compound of formula (I)

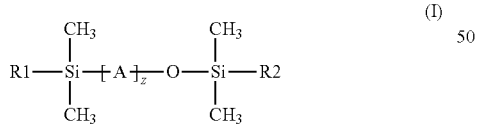

where
A=

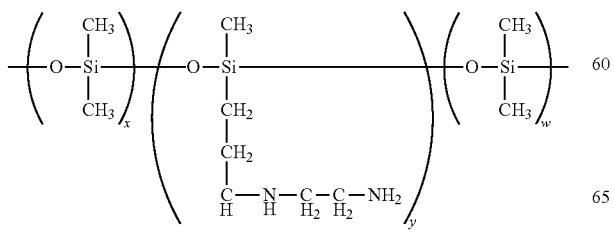

Wherein x and y independently stand for numbers from 1 to 100; w stands for a number from 0 to 100; z stands for a number from 1 to 100, where, if z≥2, the respective values x, y, and w in a structural element A may be selected in each case independently of preceding structural elements A; and R1 and R2 independently stand for a linear or branched, saturated, unsaturated, or multiply unsaturated $C_5$-$C_{20}$ alkyl group, a hydroxy group, a $C_1$-$C_{30}$ alkoxy group, a carboxy-$C_1$-$C_{30}$ alkyl group, or a $C_1$-$C_6$ alkyl-(O—$CH_2$—$CH_2$)$_n$—O— group, wherein n stands for an integer from 1 to 60.

The agents of the present invention provide a hair treatment product by means of which an intense, natural luster may be produced on the hair which is long-lasting and also does not diminish after repeated hair washings. Even after multiple shampoos, the hair can have just as much luster as directly after the treatment with the luster-producing agent.

It has surprisingly now been found that cosmetic agents that contain a particular combination of at least one inorganic and/or organic acid, a direct dye, and a specific aminosilicone produce a particularly long-lasting luster on hair.

Furthermore, other desirable features and characteristics of the present invention will become apparent from the subsequent detailed description of the invention and the appended claims, taken in conjunction with the accompanying drawings and this background of the invention.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the present invention relates to an agent for treating keratinic fibers, in particular human hair, which is characterized in that the agent contains in a cosmetically suitable carrier a) at least one inorganic and/or organic acid
b) at least one direct dye and
c) at least one compound of formula (I)
where

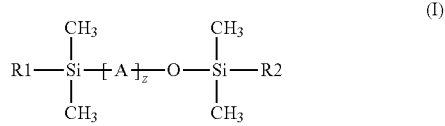

A=

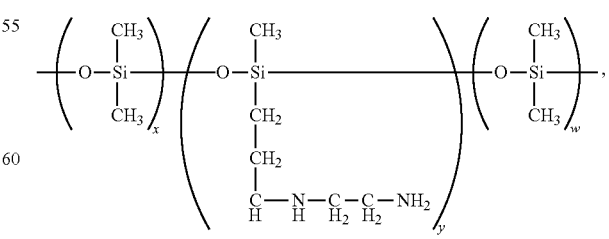

wherein
i. x and y independently stand for numbers from 1 to 100,
ii. w stands for a number from 0 to 100, iii. z stands for a number from 1 to 100, where, if z≥2, the respective values x, y, and w in a structural element A may be selected in each case independently of preceding structural elements A, and iv. R1 and R2 independently stand for a linear or branched, saturated, unsaturated, or multiply unsaturated $C_5$-$C_{20}$ alkyl group, a hydroxy group, a $C_1$-$C_{30}$ alkoxy group, a carboxy-$C_1$-$C_{30}$ alkyl group, or a $C_1$-$C_6$ alkyl-(O—$CH_2$—$CH_2$)$_n$—O— group, where n stands for an integer from 1 to 60.

Keratinic fibers are understood to mean wool, fur, feathers, and in particular human hair. In principle, however, the coloring agents according to the invention may also be used for coloring other natural fibers, for example cotton, jute, sisal, linen, or silk, modified dye natural fibers such as regenerated cellulose, nitro cellulose, alkyl cellulose, or hydroxyalkyl cellulose, or acetyl cellulose.

In the sense of the invention, "long-lasting luster" is intended to mean the luster of the keratinic fibers after multiple hair washings, in particular after three hair washings.

The agents according to the invention contain the acid(s) a), the direct dye(s) b), and the compound(s) of formula (I) c) in a cosmetic carrier, preferably in a suitable aqueous, alcoholic, or aqueous-alcoholic carrier. For the purposes of the hair treatment, such carriers are, for example, creams, emulsions, gels, or also surfactant-containing foaming solutions such as shampoos, aerosol foams, foam formulations, or other preparations that are suitable for applying to the hair. However, it is also conceivable to integrate the ingredients a), b), and c) into a powdered or also a tablet formulation, and to admix these ingredients with an aqueous or aqueous-alcoholic carrier prior to application.

As the first important formulation component, the agent according to the invention for treating keratinic fibers contains at least one inorganic and/or organic acid a). All compounds which are able to deliver one proton (monobasic acid) or multiple protons (polybasic acid) are suitable in principle as acids. Mineral acids, for example, such as hydrochloric acid, sulfuric acid, and phosphoric acid, preferably in their form diluted with water, may be used as inorganic acids. Within the group of the inorganic acids, sulfuric acid and phosphoric acid are preferred. Phosphoric acid is very particularly preferred.

Organic acids may also be used in the formulations according to the invention. Typical representatives of organic acids are aliphatic mono- and dicarboxylic acids such as acetic acid, propionic acid, oxalic acid, and 1,3-propanedioic acid, in addition to carboxylic acids such as benzoic acid. Further organic acids according to the invention are hydroxycarboxylic acids such as glycolic acid, citric acid, tartaric acid, malic acid, and lactic acid. In addition, unsaturated mono- or dicarboxylic acids such as fumaric acid or α-ketocarboxylic acids, for example pyruvic acid (2-oxopropionic acid), conform to the invention.

Mono- or diphosphonic acids may also be used to achieve the object according to the invention. One example of a preferred diphosphonic acid is 1-hydroxyethane-1,1-diphosphonic acid. Heterocyclic mono- and dicarboxylic acids such as pyridine-2-carboxylic acid, pyridine-3-carboxylic acid, pyridine-4-carboxylic acid. and pyridine-2,6-dicarboxylic acid likewise show very good suitability for producing hair treatment products with a long-lasting luster. However, due to the technical formulation and regulatory requirements which exist for cosmetic agents, low-odor acids which are approved for use in cosmetics are most suitable for developing hair treatment products with long-lasting luster. Hair treatment products which contain at least one acid selected from citric acid, tartaric acid, malic acid, lactic acid, 1-hydroxyethane-1,1-diphosphonic acid, 2,6-dipicolinic acid, and benzoic acid are therefore preferred.

One preferred embodiment is an agent for treating keratinic fibers, which is characterized in that the agent contains at least one acid selected from citric acid, tartaric acid, malic acid, lactic acid, 1-hydroxyethane-1,1-diphosphonic acid, 2,6-dipicolinic acid, and benzoic acid as the inorganic and/or organic acid.

Within this group, the acids citric acid, tartaric acid, malic acid, and lactic acid are once again explicitly mentioned as being very particularly suited. Thus, it is very particularly preferred that the agent according to the invention contains at least one acid selected from citric acid, tartaric acid, malic acid, and lactic acid as acid a).

The inorganic and/or organic acids, depending on their acid strength and buffer substances or alkaline reacting compounds which are optionally additionally contained, may be contained in the agent in a total quantity of 0.001 to 15 wt.-%, preferably 0.005 to 12 wt.-%, more preferably 0.01 to 9 wt.-%, and particularly preferably 0.1 to 6 wt.-%, the weight percentages in each case referring to the total quantity of the agent.

As the result of proton cleavage, in the presence of water the acids increase the concentration of $H^+$ and $H_3O^+$ ions, which is associated with a drop in the pH. In the course of the studies leading to the present invention, it has been shown that the concentration of the acids contained in the agent, and therefore also the pH, significantly influences the intensity of the producible luster. The keratinic fibers then have a particularly intense and long-lasting luster when the agent according to the invention which is applied thereto has a pH of less than 7.

It is therefore advantageous when the agent according to the invention has a pH of 2 to 7, preferably 3 to 6.9, more preferably 4 to 6.8, and in particular preferably 5 to 6.7.

Measured pH values, in the sense of the present invention, are pH values that have been measured at a temperature of 22° C. Glass electrodes are particularly suited for measuring the pH.

A further preferred embodiment, therefore, is an agent for treating keratinic fibers, which is characterized in that the agent has a pH of 2 to 7, preferably 3 to 6.9, more preferably 4 to 6.8, and in particular preferably 5 to 6.7, at a temperature of 22° C.

The agents according to the invention may additionally contain buffers or buffer systems for stabilizing the particular desired pH. By definition, buffer systems are solutions of a weak acid with a practically completely dissociated salt of the same acid.

Buffers according to the invention may be composed of a weak inorganic and/or organic acid a) which is used in a mixture with its salt. However, it is likewise possible for the agent according to the invention to contain a strong inorganic and/or organic acid a), and in addition, for the mixture of a weak acid and its salt to be added to the agent as a buffer. The salts of the weak acids may be the alkali salts, preferably the sodium and potassium salts, of the weak acids.

Examples of buffer systems according to the invention include acetic acid/sodium acetate, acetic acid/potassium acetate, citric acid/sodium citrate, citric acid/potassium citrate, tartaric acid/sodium tartrate, tartaric acid/potassium tartrate, lactic acid/sodium lactate, and lactic acid/potassium lactate.

As the second important ingredient, the agent according to the invention for treating keratinic fibers contains at least one direct dye b). Direct dyes are dyes which are absorbed directly onto the hair and which require no oxidative process for forming the color. Direct dyes are customarily nitrophenylenediamines, nitroaminophenols, azo dyes, anthraquinones, or indophenols.

Direct dyes may be classified as anionic, cationic, and nonionic direct dyes. The direct dyes may be contained in the agent in a total quantity of 0.0001 to 5 wt.-%, preferably 0.001 to 2.5 wt.-%, more preferably 0.01 to 1 wt.-%, and particularly preferably 0.02 to 0.25 wt.-%, based on the total weight of the agent.

In one particularly preferred embodiment, the direct dyes contained in the agent according to the invention do not result in a strong coloration of the keratinic fibers, but, rather, result in slight shading which enhances the luster. In this case, the total quantity of all direct dyes contained in the agent according to the invention is less than 1 wt.-%, preferably less than 0.5 wt.-%, and particularly preferably less than 0.25 wt.-%, based on the total weight of the agent.

A further preferred embodiment, therefore, is an agent for treating keratinic fibers which is characterized in that the agent contains one or more direct dyes in a total quantity of 0.0001 to 5 wt.-%, preferably 0.001 to 2.5 wt.-%, more preferably 0.01 to 1 wt.-%, and particularly preferably 0.02 to 0.25 wt.-%, based on the total weight of the agent.

Suitable anionic direct dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

Suitable cationic direct dyes are cationic triphenylmethane dyes such as Basic Blue 7, Basic Blue 26, Basic Violet 2, and Basic Violet 14, aromatic systems that are substituted with a quaternary nitrogen group, such as Basic Yellow 57, Basic Red 76, Basic Blue 99, Basic Brown 16, and Basic Brown 17, cationic anthraquinone dyes such as HC Blue 16 (Bluequat B), and direct dyes that contain a heterocycle having at least one quaternary nitrogen atom, in particular Basic Yellow 87, Basic Orange 31, and Basic Red 51. The cationic direct dyes, which are marketed under the trademark Arianor, are cationic direct dyes which are likewise suitable according to the invention.

In particular nonionic nitro dyes and quinone dyes, and neutral azo dyes, are suited as nonionic direct dyes. Suitable nonionic direct dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, in addition to 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxalin, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

The agents according to the invention may contain all conceivable combinations of the above-mentioned direct dyes. However, certain dye combinations have proven to be particularly advantageous with regard to long-lasting luster production.

The agent according to the invention preferably contains a nonionic dye as direct dye b). The agent according to the invention very particularly preferably contains a nonionic nitro dye as direct dye b).

Accordingly, agents are particularly preferred which contain a) at least one inorganic and/or organic acid
b) at least one direct dye from the group of nonionic nitro dyes and
c) at least one compound of formula (I).

Another preferred embodiment, therefore, is an agent for treating keratinic fibers which is characterized in that the agent contains at least one nonionic nitro dye as direct dye.

By definition, nonionic nitro dyes are substituted nitrobenzene derivatives. These nitrobenzene derivatives may be substituted, for example, with one or more substituents selected from an amino group, a hydroxy group, a $C_1$-$C_6$ alkyl group, a $C_1$-$C_6$ alkylamino group, a $C_1$-$C_6$ dialkylamino group, a $C_1$-$C_6$ alkoxy group, a halogen atom, a hydroxy-$C_2$-$C_6$ alkylamino group, or a bis(hydroxy-$C_2$-$C_6$ alkyl)amino group.

Furthermore, particular combinations of nonionic nitro dyes have proven to be particularly suitable with regard to producing an optimal color and luster result.

A further preferred embodiment, therefore, is an agent which contains one of the following combinations of direct dyes: HC Blue 12/HC Yellow 2, HC Blue 12/HC Yellow 4, HC Blue 12/HC Yellow 5, HC Blue 12/HC Yellow 6, HC Blue 12/HC Yellow 12, HC Blue 12/HC Orange 1, HC Blue 12/HC Red 1, HC Blue 12/HC Red 3, HC Blue 12/HC Red 7, HC Blue 12/HC Red 10, HC Blue 12/HC Red 11, HC Blue 12/HC Red 13, HC Blue 12/HC Red BN, HC Blue 12/HC Violet 1, HC Blue 12/1,4-diamino-2-nitrobenzene, HC Blue 12/2-amino-4-nitrophenol, HC Blue 12/1,4-bis-(2-hydroxyethyl)amino-2-nitrobenzene, HC Blue 12/3-nitro-4-(2-hydroxyethyl)aminophenol, HC Blue 12/4-[(2-hydroxyethyl)amino]-3-nitro-1-methylbenzene, HC Blue 12/1-amino-4-(2-hydroxyethyl)amino-5-chloro-2-nitrobenzene, HC Blue 12/1-amino-4-(2-hydroxyethyl)amino-5-chloro-2-nitrobenzene, HC Blue 12/4-amino-3-nitrophenol, HC Blue 12/4-[(3-hydroxypropyl)amino]-3-nitrophenol, HC Blue 12/2-amino-6-chloro-4-nitrophenol, HC Blue 12/4-ethylamino-3-nitrobenzoic acid, or HC Blue 12/2-chloro-6-ethylamino-4-nitrophenol.

A likewise preferred embodiment is an agent which contains one of the following combinations of direct dyes: HC Yellow 2/HC Yellow 4, HC Yellow 2/HC Yellow 5, HC Yellow 2/HC Yellow 6, HC Yellow 2/HC Yellow 12, HC Yellow 2/HC Orange 1, HC Yellow 2/HC Red 1, HC Yellow 2/HC Red 3, HC Yellow 2/HC Red 7, HC Yellow 2/HC Red 10, HC Yellow 2/HC Red 11, HC Yellow 2/HC Red 13, HC Yellow 2/HC Red BN, HC Yellow 2/HC Violet 1, HC Yellow 2/HC Blue 2, HC Yellow 2/HC Blue 11, HC Yellow 2/HC Blue 12, HC Yellow 2/1,4-diamino-2-nitrobenzene, HC Yellow 2/2-amino-4-nitrophenol, HC Yellow 2/1,4-bis-(2-hydroxyethyl)amino-2-nitrobenzene, HC Yellow 2/3-nitro-4-(2-hydroxyethyl)aminophenol, HC Yellow 2/4-[(2-hydroxyethyl)amino]-3-nitro-1-methylbenzene, HC Yellow 2/1-amino-4-(2-hydroxyethyl)amino-5-chloro-2-nitrobenzene, HC Yellow 2/4-amino-3-nitrophenol, HC Yellow 2/4-

[(3-hydroxypropyl)amino]-3-nitrophenol, HC Yellow 2/2-amino-6-chloro-4-nitrophenol, HC Yellow 2/4-ethylamino-3-nitrobenzoic acid, or HC Yellow 2/2-chloro-6-ethylamino-4-nitrophenol.

A likewise preferred embodiment is an agent which contains one of the following combinations of direct dyes: 2-amino-6-chloro-4-nitrophenol/HC Yellow 2, 2-amino-6-chloro-4-nitrophenol/HC Yellow 4, 2-amino-6-chloro-4-nitrophenol/HC Yellow 5, 2-amino-6-chloro-4-nitrophenol/HC Yellow 6, 2-amino-6-chloro-4-nitrophenol/HC Yellow 12, 2-amino-6-chloro-4-nitrophenol/HC Orange 1, 2-amino-6-chloro-4-nitrophenol/HC Red 1, 2-amino-6-chloro-4-nitrophenol/HC Red 3, 2-amino-6-chloro-4-nitrophenol/HC Red 7, 2-amino-6-chloro-4-nitrophenol/HC Red 10, 2-amino-6-chloro-4-nitrophenol/HC Red 11, 2-amino-6-chloro-4-nitrophenol/HC Red 13, 2-amino-6-chloro-4-nitrophenol/HC Red BN, 2-amino-6-chloro-4-nitrophenol/HC Blue 2, 2-amino-6-chloro-4-nitrophenol/HC Blue 11,2-amino-6-chloro-4-nitrophenol/HC Blue 12,2-amino-6-chloro-4-nitrophenol/HC Violet 1, 2-amino-6-chloro-4-nitrophenol/1,4-diamino-2-nitrobenzene, 2-amino-6-chloro-4-nitrophenol/2-amino-4-nitrophenol, 2-amino-6-chloro-4-nitrophenol/1,4-bis-(2-hydroxyethyl)amino-2-nitrobenzene, 2-amino-6-chloro-4-nitrophenol/3-nitro-4-(2-hydroxyethyl)aminophenol, 2-amino-6-chloro-4-nitrophenol/4-[(2-hydroxyethyl)amino]-3-nitro-1-methylbenzene, 2-amino-6-chloro-4-nitrophenol/1-amino-4-(2-hydroxyethyl)amino-5-chloro-2-nitrobenzene, 2-amino-6-chloro-4-nitrophenol/4-amino-3-nitrophenol, 2-amino-6-chloro-4-nitrophenol/4-[(3-hydroxypropyl)amino]-3-nitrophenol, 2-amino-6-chloro-4-nitrophenol/4-ethylamino-3-nitrobenzoic acid, or 2-amino-6-chloro-4-nitrophenol/2-chloro-6-ethylamino-4-nitrophenol.

A further preferred embodiment, therefore, is an agent for treating keratinic fibers which is characterized in that the agent contains one of the following combinations of direct dyes: HC Blue 12/HC Yellow 2, HC Blue 12/HC Yellow 4, HC Blue 12/HC Yellow 5, HC Blue 12/HC Yellow 6, HC Blue 12/HC Yellow 12, HC Blue 12/HC Orange 1, HC Blue 12/HC Red 1, HC Blue 12/HC Red 3, HC Blue 12/HC Red 7, HC Blue 12/HC Red 10, HC Blue 12/HC Red 11, HC Blue 12/HC Red 13, HC Blue 12/HC Red BN, HC Blue 12/HC Violet 1, HC Blue 12/1,4-diamino-2-nitrobenzene, HC Blue 12/2-amino-4-nitrophenol, HC Blue 12/1,4-bis-(2-hydroxyethyl)amino-2-nitrobenzene, HC Blue 12/3-nitro-4-(2-hydroxyethyl)aminophenol, HC Blue 12/4-[(2-hydroxyethyl)amino]-3-nitro-1-methylbenzene, HC Blue 12/1-amino-4-(2-hydroxyethyl)amino-5-chloro-2-nitrobenzene, HC Blue 12/1-amino-4-(2-hydroxyethyl)amino-5-chloro-2-nitrobenzene, HC Blue 12/4-amino-3-nitrophenol, HC Blue 12/4-[(3-hydroxypropyl)amino]-3-nitrophenol, HC Blue 12/2-amino-6-chloro-4-nitrophenol, HC Blue 12/4-ethylamino-3-nitrobenzoic acid, HC Blue 12/2-chloro-6-ethylamino-4-nitrophenol, HC Yellow 2/HC Yellow 4, HC Yellow 2/HC Yellow 5, HC Yellow 2/HC Yellow 6, HC Yellow 2/HC Yellow 12, HC Yellow 2/HC Orange 1, HC Yellow 2/HC Red 1, HC Yellow 2/HC Red 3, HC Yellow 2/HC Red 7, HC Yellow 2/HC Red 10, HC Yellow 2/HC Red 11, HC Yellow 2/HC Red 13, HC Yellow 2/HC Red BN, HC Yellow 2/HC Violet 1, HC Yellow 2/HC Blue 2, HC Yellow 2/HC Blue 11, HC Yellow 2/HC Blue 12, HC Yellow 2/1,4-diamino-2-nitrobenzene, HC Yellow 2/2-amino-4-nitrophenol, HC Yellow 2/1,4-bis-(2-hydroxyethyl)amino-2-nitrobenzene, HC Yellow 2/3-nitro-4-(2-hydroxyethyl)aminophenol, HC Yellow 2/4-[(2-hydroxyethyl)amino]-3-nitro-1-methylbenzene, HC Yellow 2/1-amino-4-(2-hydroxyethyl)amino-5-chloro-2-nitrobenzene, HC Yellow 2/4-amino-3-nitrophenol, HC Yellow 2/4[(3-hydroxypropyl)amino]-3-nitrophenol, HC Yellow 2/2-amino-6-chloro-4-nitrophenol, HC Yellow 2/4-ethylamino-3-nitrobenzoic acid or HC Yellow 2/2-chloro-6-ethylamino-4-nitrophenol, 2-amino-6-chloro-4-nitrophenol/HC Yellow 2, 2-amino-6-chloro-4-nitrophenol/HC Yellow 4, 2-amino-6-chloro-4-nitrophenol/HC Yellow 5, 2-amino-6-chloro-4-nitrophenol/HC Yellow 6, 2-amino-6-chloro-4-nitrophenol/HC Yellow 12, 2-amino-6-chloro-4-nitrophenol/HC Orange 1, 2-amino-6-chloro-4-nitrophenol/HC Red 1, 2-amino-6-chloro-4-nitrophenol/HC Red 3,2-amino-6-chloro-4-nitrophenol/HC Red 7, 2-amino-6-chloro-4-nitrophenol/HC Red 10, 2-amino-6-chloro-4-nitrophenol/HC Red 11, 2-amino-6-chloro-4-nitrophenol/HC Red 13, 2-amino-6-chloro-4-nitrophenol/HC Red BN, 2-amino-6-chloro-4-nitrophenol/HC Blue 2, 2-amino-6-chloro-4-nitrophenol/HC Blue 11, 2-amino-6-chloro-4-nitrophenol/HC Blue 12, 2-amino-6-chloro-4-nitrophenol/HC Violet 1, 2-amino-6-chloro-4-nitrophenol/1,4-diamino-2-nitrobenzene, 2-amino-6-chloro-4-nitrophenol/2-amino-4-nitrophenol, 2-amino-6-chloro-4-nitrophenol/1,4-bis-(2-hydroxyethyl)amino-2-nitrobenzene, 2-amino-6-chloro-4-nitrophenol/3-nitro-4-(2-hydroxyethyl)aminophenol, 2-amino-6-chloro-4-nitrophenol/4-[(2-hydroxyethyl)amino]-3-nitro-1-methylbenzene, 2-amino-6-chloro-4-nitrophenol/1-amino-4-(2-hydroxyethyl)amino-5-chloro-2-nitrobenzene, 2-amino-6-chloro-4-nitrophenol/4-amino-3-nitrophenol, 2-amino-6-chloro-4-nitrophenol/4-[(3-hydroxypropyl)amino]-3-nitrophenol, 2-amino-6-chloro-4-nitrophenol/4-ethylamino-3-nitrobenzoic acid, or 2-amino-6-chloro-4-nitrophenol/2-chloro-6-ethylamino-4-nitrophenol.

Specifically, it is very particularly preferred when the agent according to the invention contains a combination of the four direct, nonionic dyes HC Yellow 2, HC Blue 12, 2-amino-6-chloro-4-nitrophenol, and N,N-bis(2-hydroxyethyl)-2-nitro-p-phenlyenediamine.

In addition, dyes occurring in nature, as contained, for example, in henna red, henna neutral, henna black, chamomile flower, sandalwood, black tea, walnut, black alder bark, sage, logwood, madder root, catechu, and alkanna root may also be used as direct dyes.

As the third important formulation component c), the agent according to the invention for treating keratinic fibers contains at least one compound of formula (I)

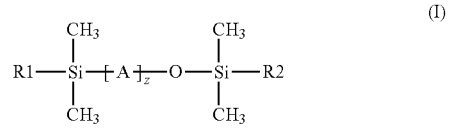

where
A=

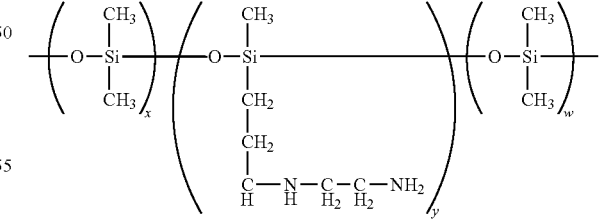

wherein
i. x and y independently stand for numbers from 1 to 100,
ii. w stands for a number from 0 to 100,
iii. z stands for a number from 1 to 100, where, if z≥2, the respective values x, y, and w in a structural element A may be selected in each case independently of preceding structural elements A,
and
iv. R1 and R2 independently stand for a linear or branched, saturated, unsaturated, or multiply unsaturated $C_5$-$C_{20}$ alkyl group, a hydroxy group, a $C_1$-$C_{30}$ alkoxy group, a carboxy-$C_1$-$C_{30}$ alkyl group, or a $C_1$-$C_6$ alkyl-(O—CH$_2$—CH$_2$)$_n$—O— group, where n stands for an integer from 1 to 60.

According to the invention, the structural elements A of the compound of formula (I) are made up of one or more {3-[(2-aminoethyl)amino]propyl}methylsiloxane elements and one or more dimethylsiloxane elements. The number of dimethylsiloxane elements is defined by the parameters x and w. The number of {3-[(2-aminoethyl)amino]propyl}methylsiloxane elements is defined by the parameter y. According to the invention, the values of the parameters x and y independently stand for numbers between 1 and 100, and according to the invention, the parameter w may stand for a number from 0 to 100.

The number of structural elements A is specified by the parameter z. According to the invention, the value of the parameter z is between 1 and 100. If z≥2, the parameters x, y, and w in each structural element A may be selected independently of preceding structural elements A. It follows that, for the case z≥2, the number of {3-[(2-aminoethyl)amino]propyl}methylsiloxane elements and/or the number of dimethylsiloxane elements in the individual structural elements A may be different from one another.

According to the present invention, the siloxane base structure of the compound(s) of formula (I) is terminated at both ends by the radicals R1 and R2, where R1 and R2 may independently stand for a linear or branched, saturated, unsaturated, or multiply unsaturated $C_5$-$C_{20}$ alkyl group, a hydroxy group, a $C_1$-$C_{30}$ alkoxy group, a carboxy-$C_1$-$C_{30}$ alkyl group, or a $C_1$-$C_6$ alkyl-(O—CH$_2$—CH$_2$)$_n$—O— group.

If R1 and/or R2 stand(s) for a branched, saturated, unsaturated, or multiply unsaturated $C_5$-$C_{20}$ alkyl radical, the siloxane structure is terminated by a fatty alkyl chain. Within the meaning of the present invention, fatty alkyl chains are all linear and/or branched, saturated and/or unsaturated and/or multiply unsaturated carbon chains, the carbon chain preferably being a $C_6$-$C_{30}$ chain, particularly preferably a $C_8$-$C_{24}$ chain, and in particular a $C_{14}$-$C_{20}$ chain. Examples of fatty alkyl chains according to the invention are hexyl, heptyl, octyl, nonyl, decyl, dodecyl, tetradecyl, pentadecyl, hexadecyl, heptadecyl, octadecyl, nonadecyl, eicosyl, docosyl, tetracosyl, hexacosyl, isostearyl, (9Z)-tetradeca-9-enyl, (9Z)-hexadeca-9-enyl, (6Z)-octadeca-6-enyl, (9Z)-octadeca-9-enyl, (9E)-octadeca-9-enyl, (11E)-octadeca-11-enyl, (9Z)-eicosa-9-enyl, (11Z)-eicosa-11-enyl, (11Z)-docosa-11-enyl, (13Z)-docosa-13-enyl, (15Z)-tetracosa-15-enyl, (9Z,12Z)-octadeca-9,12-dienyl, (9Z,12Z,15Z)-octadeca-9,12,15-trienyl, (6Z,9Z,12Z)-octadeca-6,9,12-trienyl, (8E,10E,12Z)-octadeca-8,10,12-trienyl, (9Z,11E,13Z)-octadeca-9,11,13-trienyl, (9Z,11E,13E)-octadeca-9,11,13-trienyl, (9E,11E,13E)-octadeca-9,11,13-trienyl, (5Z,8Z,11Z,14Z)-eicosa-5,8,11,14-tetraenyl, (5Z,8Z,11Z,14Z,17Z)-eicosa-5,8,11,14,17-pentaenyl, (7Z,10Z,13Z,16Z,19Z)-docosa-7,10,13,16,19-pentaenyl, and (4Z,7Z,10Z,13Z,16Z,19Z)-docosa-4,7,10,13,16,19-hexaenyl.

In one preferred embodiment of the invention, the radicals R1 and R2 independently stand for linear alkyl chains, preferably $C_{14}$-$C_{20}$ alkyl, particularly preferably tetradecyl, pentadecyl, hexadecyl, heptadecyl, octadecyl, nonadecyl, or eicosyl. Hexadecyl (cetyl) and/or octadecyl (stearyl) are particularly preferred. "Cetearyl" is understood to mean a mixture of cetyl and stearyl, this mixture likewise being preferred.

In another preferred embodiment, an agent according to the invention is therefore characterized in that the agent according to the invention contains a compound of formula (I) in which the substituents R1 and R2 independently stand for a linear or branched, saturated, unsaturated, or multiply unsaturated $C_5$-$C_{20}$ alkyl chain, preferably for a linear $C_{14}$-$C_{20}$ alkyl chain, particularly preferably for a representative from the group H$_3$C—(CH$_2$)$_{13}$—, H$_3$C—(CH$_2$)$_{15}$—, H$_3$C—(CH$_2$)$_{17}$—, H$_3$C—(CH$_2$)$_{19}$—.

According to the invention, compounds of formula (I) are particularly preferred in which the radicals R1 and R2 independently stand for H$_3$C—(CH$_2$)$_{15}$— or H$_3$C—(CH$_2$)$_{17}$—. In this case, the amodimethicone according to the invention is a bis-cetearyl amodimethicone.

Agents are particularly preferred which contain
a) at least one inorganic and/or organic acid
b) at least one direct dye from the group of nonionic nitro dyes and
c) at least one bis-cetearyl amodimethicone.

In another preferred embodiment, an agent according to the invention is therefore characterized in that it contains a compound of formula (I), in which R1 stands for H$_3$C—(CH$_2$)$_{15}$— or H$_3$C—(CH$_2$)$_{17}$—, and R2 stands for H$_3$C—(CH$_2$)$_{15}$— or H$_3$C—(CH$_2$)$_{17}$—. Such compounds are known under the INCI name bis-cetearyl amodimethicone.

The compound(s) of formula (I) may be contained in the agent according to the invention in a total quantity of 0.005 to 5 wt.-%, preferably 0.1 to 4.5 wt.-%, particularly preferably 1 to 3 wt.-%, and in particular preferably 1.5 to 2.5 wt.-%, based on the total weight of the agent.

In another embodiment, the agent according to the invention is characterized in that it contains the compound or the compounds of formula (I) in a total quantity of 0.005 to 5 wt.-%, preferably 0.1 to 4.5 wt.-%, particularly preferably 1 to 3 wt.-%, and in particular preferably 1.5 to 2.5 wt.-%, based on the total weight of the agent.

The compositions of several preferred hair treatment products according to the invention are listed in the following tables (all data are expressed in wt.-%, based on the total weight of the agent):

| No. | a) Inorganic/organic acid | b) Direct dye | c) Compound(s) of formula (I) | pH of agent |
|---|---|---|---|---|
| 1 | Citric acid | 0.0001 to 5 wt.-% | 0.005 to 5 wt.-% | 7.0-6.5 |
| 2 | Citric acid | 0.001 to 2.5 wt.-% | 0.005 to 5 wt.-% | 7.0-6.5 |
| 3 | Citric acid | 0.01 to 1 wt.-% | 0.005 to 5 wt.-% | 7.0-6.5 |
| 4 | Citric acid | 0.02 to 0.25 wt.-% | 0.005 to 5 wt.-% | 7.0-6.5 |
| 5 | Citric acid | 0.0001 to 5 wt.-% | 0.005 to 5 wt.-% | 6.5-6.0 |
| 6 | Citric acid | 0.001 to 2.5 wt.-% | 0.005 to 5 wt.-% | 6.5-6.0 |
| 7 | Citric acid | 0.01 to 1 wt.-% | 0.005 to 5 wt.-% | 6.5-6.0 |
| 8 | Citric acid | 0.02 to 0.25 wt.-% | 0.005 to 5 wt.-% | 6.5-6.0 |
| 9 | Citric acid | 0.0001 to 5 wt.-% | 0.005 to 5 wt.-% | 6.0-5.5 |
| 10 | Citric acid | 0.001 to 2.5 wt.-% | 0.005 to 5 wt.-% | 6.0-5.5 |
| 11 | Citric acid | 0.01 to 1 wt.-% | 0.005 to 5 wt.-% | 6.0-5.5 |

-continued

| No. | a) Inorganic/ organic acid | b) Direct dye | c) Compound(s) of formula (I) | pH of agent |
|---|---|---|---|---|
| 12 | Citric acid | 0.02 to 0.25 wt.-% | 0.005 to 5 wt.-% | 6.0-5.5 |
| 13 | Citric acid | 0.0001 to 5 wt.-% | 0.005 to 5 wt.-% | 5.5-5.0 |
| 14 | Citric acid | 0.001 to 2.5 wt.-% | 0.005 to 5 wt.-% | 5.5-5.0 |
| 15 | Citric acid | 0.01 to 1 wt.-% | 0.005 to 5 wt.-% | 5.5-5.0 |
| 16 | Citric acid | 0.02 to 0.25 wt.-% | 0.005 to 5 wt.-% | 5.5-5.0 |
| 17 | Tartaric acid | 0.0001 to 5 wt.-% | 0.005 to 5 wt.-% | 7.0-6.5 |
| 18 | Tartaric acid | 0.001 to 2.5 wt.-% | 0.005 to 5 wt.-% | 7.0-6.5 |
| 19 | Tartaric acid | 0.01 to 1 wt.-% | 0.005 to 5 wt.-% | 7.0-6.5 |
| 20 | Tartaric acid | 0.02 to 0.25 wt.-% | 0.005 to 5 wt.-% | 7.0-6.5 |
| 21 | Tartaric acid | 0.0001 to 5 wt.-% | 0.005 to 5 wt.-% | 6.5-6.0 |
| 22 | Tartaric acid | 0.001 to 2.5 wt.-% | 0.005 to 5 wt.-% | 6.5-6.0 |
| 23 | Tartaric acid | 0.01 to 1 wt.-% | 0.005 to 5 wt.-% | 6.5-6.0 |
| 24 | Tartaric acid | 0.02 to 0.25 wt.-% | 0.005 to 5 wt.-% | 6.5-6.0 |
| 25 | Tartaric acid | 0.0001 to 5 wt.-% | 0.005 to 5 wt.-% | 6.0-5.5 |
| 26 | Tartaric acid | 0.001 to 2.5 wt.-% | 0.005 to 5 wt.-% | 6.0-5.5 |
| 27 | Tartaric acid | 0.01 to 1 wt.-% | 0.005 to 5 wt.-% | 6.0-5.5 |
| 28 | Tartaric acid | 0.02 to 0.25 wt.-% | 0.005 to 5 wt.-% | 6.0-5.5 |
| 29 | Tartaric acid | 0.0001 to 5 wt.-% | 0.005 to 5 wt.-% | 5.5-5.0 |
| 30 | Tartaric acid | 0.001 to 2.5 wt.-% | 0.005 to 5 wt.-% | 5.5-5.0 |
| 31 | Tartaric acid | 0.01 to 1 wt.-% | 0.005 to 5 wt.-% | 5.5-5.0 |
| 32 | Tartaric acid | 0.02 to 0.25 wt.-% | 0.005 to 5 wt.-% | 5.5-5.0 |
| 33 | Malic acid | 0.0001 to 5 wt.-% | 0.005 to 5 wt.-% | 7.0-6.5 |
| 34 | Malic acid | 0.001 to 2.5 wt.-% | 0.005 to 5 wt.-% | 7.0-6.5 |
| 35 | Malic acid | 0.01 to 1 wt.-% | 0.005 to 5 wt.-% | 7.0-6.5 |
| 36 | Malic acid | 0.02 to 0.25 wt.-% | 0.005 to 5 wt.-% | 7.0-6.5 |
| 37 | Malic acid | 0.0001 to 5 wt.-% | 0.005 to 5 wt.-% | 6.5-6.0 |
| 38 | Malic acid | 0.001 to 2.5 wt.-% | 0.005 to 5 wt.-% | 6.5-6.0 |
| 39 | Malic acid | 0.01 to 1 wt.-% | 0.005 to 5 wt.-% | 6.5-6.0 |
| 40 | Malic acid | 0.02 to 0.25 wt.-% | 0.005 to 5 wt.-% | 6.5-6.0 |
| 41 | Malic acid | 0.0001 to 5 wt.-% | 0.005 to 5 wt.-% | 6.0-5.5 |
| 42 | Malic acid | 0.001 to 2.5 wt.-% | 0.005 to 5 wt.-% | 6.0-5.5 |
| 43 | Malic acid | 0.01 to 1 wt.-% | 0.005 to 5 wt.-% | 6.0-5.5 |
| 44 | Malic acid | 0.02 to 0.25 wt.-% | 0.005 to 5 wt.-% | 6.0-5.5 |
| 45 | Malic acid | 0.0001 to 5 wt.-% | 0.005 to 5 wt.-% | 5.5-5.0 |
| 46 | Malic acid | 0.001 to 2.5 wt.-% | 0.005 to 5 wt.-% | 5.5-5.0 |
| 47 | Malic acid | 0.01 to 1 wt.-% | 0.005 to 5 wt.-% | 5.5-5.0 |
| 48 | Malic acid | 0.02 to 0.25 wt.-% | 0.005 to 5 wt.-% | 5.5-5.0 |
| 49 | Lactic acid | 0.0001 to 5 wt.-% | 0.005 to 5 wt.-% | 7.0-6.5 |
| 50 | Lactic acid | 0.001 to 2.5 wt.-% | 0.005 to 5 wt.-% | 7.0-6.5 |
| 51 | Lactic acid | 0.01 to 1 wt.-% | 0.005 to 5 wt.-% | 7.0-6.5 |
| 52 | Lactic acid | 0.02 to 0.25 wt.-% | 0.005 to 5 wt.-% | 7.0-6.5 |
| 53 | Lactic acid | 0.0001 to 5 wt.-% | 0.005 to 5 wt.-% | 6.5-6.0 |
| 54 | Lactic acid | 0.001 to 2.5 wt.-% | 0.005 to 5 wt.-% | 6.5-6.0 |
| 55 | Lactic acid | 0.01 to 1 wt.-% | 0.005 to 5 wt.-% | 6.5-6.0 |
| 56 | Lactic acid | 0.02 to 0.25 wt.-% | 0.005 to 5 wt.-% | 6.5-6.0 |
| 57 | Lactic acid | 0.0001 to 5 wt.-% | 0.005 to 5 wt.-% | 6.0-5.5 |
| 58 | Lactic acid | 0.001 to 2.5 wt.-% | 0.005 to 5 wt.-% | 6.0-5.5 |
| 59 | Lactic acid | 0.01 to 1 wt.-% | 0.005 to 5 wt.-% | 6.0-5.5 |
| 60 | Lactic acid | 0.02 to 0.25 wt.-% | 0.005 to 5 wt.-% | 6.0-5.5 |
| 61 | Lactic acid | 0.0001 to 5 wt.-% | 0.005 to 5 wt.-% | 5.5-5.0 |
| 62 | Lactic acid | 0.001 to 2.5 wt.-% | 0.005 to 5 wt.-% | 5.5-5.0 |
| 63 | Lactic acid | 0.01 to 1 wt.-% | 0.005 to 5 wt.-% | 5.5-5.0 |
| 64 | Lactic acid | 0.02 to 0.25 wt.-% | 0.005 to 5 wt.-% | 5.5-5.0 |
| 65 | 1-Hydroxyethane-1,1-diphosphonic acid | 0.0001 to 5 wt.-%. | 0.005 to 5 wt.-% | 7.0-6.5 |
| 66 | 1-Hydroxyethane-1,1-diphosphonic acid | 0.001 to 2.5 wt.-%. | 0.005 to 5 wt.-% | 7.0-6.5 |
| 67 | 1-Hydroxyethane-1,1-diphosphonic acid | 0.01 to 1 wt.-% | 0.005 to 5 wt.-% | 7.0-6.5 |
| 68 | 1-Hydroxyethane-1,1-diphosphonic acid | 0.02 to 0.25 wt.-% | 0.005 to 5 wt.-% | 7.0-6.5 |

-continued

| No. | a) Inorganic/ organic acid | b) Direct dye | c) Compound(s) of formula (I) | pH of agent |
|---|---|---|---|---|
| 69 | 1-Hydroxyethane-1,1-diphosphonic acid | 0.0001 to 5 wt.-%. | 0.005 to 5 wt.-% | 6.5-6.0 |
| 70 | 1-Hydroxyethane-1,1-diphosphonic acid | 0.001 to 2.5 wt.-% | 0.005 to 5 wt.-% | 6.5-6.0 |
| 71 | 1-Hydroxyethane-1,1-diphosphonic acid | 0.01 to 1 wt.-% | 0.005 to 5 wt.-% | 6.5-6.0 |
| 72 | 1-Hydroxyethane-1,1-diphosphonic acid | 0.02 to 0.25 wt.-% | 0.005 to 5 wt.-% | 6.5-6.0 |
| 73 | 1-Hydroxyethane-1,1-diphosphonic acid | 0.0001 to 5 wt.-%. | 0.005 to 5 wt.-% | 6.0-5.5 |
| 74 | 1-Hydroxyethane-1,1-diphosphonic acid | 0.001 to 2.5 wt.-%. | 0.005 to 5 wt.-% | 6.0-5.5 |
| 75 | 1-Hydroxyethane-1,1-diphosphonic acid | 0.01 to 1 wt.-% | 0.005 to 5 wt.-% | 6.0-5.5 |
| 76 | 1-Hydroxyethane-1,1-diphosphonic acid | 0.02 to 0.25 wt.-% | 0.005 to 5 wt.-% | 6.0-5.5 |
| 77 | 1-Hydroxyethane-1,1-diphosphonic acid | 0.0001 to 5 wt.-%. | 0.005 to 5 wt.-% | 5.5-5.0 |
| 78 | 1-Hydroxyethane-1,1-diphosphonic acid | 0.001 to 2.5 wt.-%. | 0.005 to 5 wt.-% | 5.5-5.0 |
| 79 | 1-Hydroxyethane-1,1-diphosphonic acid | 0.01 to 1 wt.-% | 0.005 to 5 wt.-% | 5.5-5.0 |
| 80 | 1-Hydroxyethane-1,1-diphosphonic acid | 0.02 to 0.25 wt.-% | 0.005 to 5 wt.-% | 5.5-5.0 |
| 81 | Citric acid | 0.0001 to 5 wt.-% | Bis-cetearyl amodimethicone | 7.0-6.5 |
| 82 | Citric acid | 0.001 to 2.5 wt.-% | Bis-cetearyl amodimethicone | 7.0-6.5 |
| 83 | Citric acid | 0.01 to 1 wt.-% | Bis-cetearyl amodimethicone | 7.0-6.5 |
| 84 | Citric acid | 0.02 to 0.25 wt.-% | Bis-cetearyl amodimethicone | 7.0-6.5 |
| 85 | Citric acid | 0.0001 to 5 wt.-% | Bis-cetearyl amodimethicone | 6.5-6.0 |
| 86 | Citric acid | 0.001 to 2.5 wt.-% | Bis-cetearyl amodimethicone | 6.5-6.0 |
| 87 | Citric acid | 0.01 to 1 wt.-% | Bis-cetearyl amodimethicone | 6.5-6.0 |
| 88 | Citric acid | 0.02 to 0.25 wt.-% | Bis-cetearyl amodimethicone | 6.5-6.0 |
| 89 | Citric acid | 0.0001 to 5 wt.-% | Bis-cetearyl amodimethicone | 6.0-5.5 |
| 90 | Citric acid | 0.001 to 2.5 wt.-% | Bis-cetearyl amodimethicone | 6.0-5.5 |
| 91 | Citric acid | 0.01 to 1 wt.-% | Bis-cetearyl amodimethicone | 6.0-5.5 |
| 92 | Citric acid | 0.02 to 0.25 wt.-% | Bis-cetearyl amodimethicone | 6.0-5.5 |
| 93 | Citric acid | 0.0001 to 5 wt.-% | Bis-cetearyl amodimethicone | 5.5-5.0 |
| 94 | Citric acid | 0.001 to 2.5 wt.-% | Bis-cetearyl amodimethicone | 5.5-5.0 |
| 95 | Citric acid | 0.01 to 1 wt.-% | Bis-cetearyl amodimethicone | 5.5-5.0 |
| 96 | Citric acid | 0.02 to 0.25 wt.-% | Bis-cetearyl amodimethicone | 5.5-5.0 |

-continued

| No. | a) Inorganic/ organic acid | b) Direct dye | c) Compound(s) of formula (I) | pH of agent |
|---|---|---|---|---|
| 97 | Tartaric acid | 0.0001 to 5 wt.-% | Bis-cetearyl amodimethicone | 7.0-6.5 |
| 98 | Tartaric acid | 0.001 to 2.5 wt.-% | Bis-cetearyl amodimethicone | 7.0-6.5 |
| 99 | Tartaric acid | 0.01 to 1 wt.-% | Bis-cetearyl amodimethicone | 7.0-6.5 |
| 100 | Tartaric acid | 0.02 to 0.25 wt.-% | Bis-cetearyl amodimethicone | 7.0-6.5 |
| 101 | Tartaric acid | 0.0001 to 5 wt.-% | Bis-cetearyl amodimethicone | 6.5-6.0 |
| 102 | Tartaric acid | 0.001 to 2.5 wt.-% | Bis-cetearyl amodimethicone | 6.5-6.0 |
| 103 | Tartaric acid | 0.01 to 1 wt.-% | Bis-cetearyl amodimethicone | 6.5-6.0 |
| 104 | Tartaric acid | 0.02 to 0.25 wt.-% | Bis-cetearyl amodimethicone | 6.5-6.0 |
| 105 | Tartaric acid | 0.0001 to 5 wt.-% | Bis-cetearyl amodimethicone | 6.0-5.5 |
| 106 | Tartaric acid | 0.001 to 2.5 wt.-% | Bis-cetearyl amodimethicone | 6.0-5.5 |
| 107 | Tartaric acid | 0.01 to 1 wt.-% | Bis-cetearyl amodimethicone | 6.0-5.5 |
| 108 | Tartaric acid | 0.02 to 0.25 wt.-% | Bis-cetearyl amodimethicone | 6.0-5.5 |
| 109 | Tartaric acid | 0.0001 to 5 wt.-% | Bis-cetearyl amodimethicone | 5.5-5.0 |
| 110 | Tartaric acid | 0.001 to 2.5 wt.-% | Bis-cetearyl amodimethicone | 5.5-5.0 |
| 111 | Tartaric acid | 0.01 to 1 wt.-% | Bis-cetearyl amodimethicone | 5.5-5.0 |
| 112 | Tartaric acid | 0.02 to 0.25 wt.-% | Bis-cetearyl amodimethicone | 5.5-5.0 |
| 113 | Malic acid | 0.0001 to 5 wt.-% | Bis-cetearyl amodimethicone | 7.0-6.5 |
| 114 | Malic acid | 0.001 to 2.5 wt.-% | Bis-cetearyl amodimethicone | 7.0-6.5 |
| 115 | Malic acid | 0.01 to 1 wt.-% | Bis-cetearyl amodimethicone | 7.0-6.5 |
| 116 | Malic acid | 0.02 to 0.25 wt.-% | Bis-cetearyl amodimethicone | 7.0-6.5 |
| 117 | Malic acid | 0.0001 to 5 wt.-% | Bis-cetearyl amodimethicone | 6.5-6.0 |
| 118 | Malic acid | 0.001 to 2.5 wt.-% | Bis-cetearyl amodimethicone | 6.5-6.0 |
| 119 | Malic acid | 0.01 to 1 wt.-% | Bis-cetearyl amodimethicone | 6.5-6.0 |
| 120 | Malic acid | 0.02 to 0.25 wt.-% | Bis-cetearyl amodimethicone | 6.5-6.0 |
| 121 | Malic acid | 0.0001 to 5 wt.-% | Bis-cetearyl amodimethicone | 6.0-5.5 |
| 122 | Malic acid | 0.001 to 2.5 wt.-% | Bis-cetearyl amodimethicone | 6.0-5.5 |
| 123 | Malic acid | 0.01 to 1 wt.-% | Bis-cetearyl amodimethicone | 6.0-5.5 |
| 124 | Malic acid | 0.02 to 0.25 wt.-% | Bis-cetearyl amodimethicone | 6.0-5.5 |
| 125 | Malic acid | 0.0001 to 5 wt.-% | Bis-cetearyl amodimethicone | 5.5-5.0 |
| 126 | Malic acid | 0.001 to 2.5 wt.-% | Bis-cetearyl amodimethicone | 5.5-5.0 |
| 127 | Malic acid | 0.01 to 1 wt.-% | Bis-cetearyl amodimethicone | 5.5-5.0 |
| 128 | Malic acid | 0.02 to 0.25 wt.-% | Bis-cetearyl amodimethicone | 5.5-5.0 |
| 129 | Lactic acid | 0.0001 to 5 wt.-% | Bis-cetearyl amodimethicone | 7.0-6.5 |
| 130 | Lactic acid | 0.001 to 2.5 wt.-% | Bis-cetearyl amodimethicone | 7.0-6.5 |
| 131 | Lactic acid | 0.01 to 1 wt.-% | Bis-cetearyl amodimethicone | 7.0-6.5 |
| 132 | Lactic acid | 0.02 to 0.25 wt.-% | Bis-cetearyl amodimethicone | 7.0-6.5 |
| 133 | Lactic acid | 0.0001 to 5 wt.-% | Bis-cetearyl amodimethicone | 6.5-6.0 |
| 134 | Lactic acid | 0.001 to 2.5 wt.-% | Bis-cetearyl amodimethicone | 6.5-6.0 |
| 135 | Lactic acid | 0.01 to 1 wt.-% | Bis-cetearyl amodimethicone | 6.5-6.0 |
| 136 | Lactic acid | 0.02 to 0.25 wt.-% | Bis-cetearyl amodimethicone | 6.5-6.0 |
| 137 | Lactic acid | 0.0001 to 5 wt.-% | Bis-cetearyl amodimethicone | 6.0-5.5 |
| 138 | Lactic acid | 0.001 to 2.5 wt.-% | Bis-cetearyl amodimethicone | 6.0-5.5 |
| 139 | Lactic acid | 0.01 to 1 wt.-% | Bis-cetearyl amodimethicone | 6.0-5.5 |
| 140 | Lactic acid | 0.02 to 0.25 wt.-% | Bis-cetearyl amodimethicone | 6.0-5.5 |
| 141 | Lactic acid | 0.0001 to 5 wt.-% | Bis-cetearyl amodimethicone | 5.5-5.0 |
| 142 | Lactic acid | 0.001 to 2.5 wt.-% | Bis-cetearyl amodimethicone | 5.5-5.0 |
| 143 | Lactic acid | 0.01 to 1 wt.-% | Bis-cetearyl amodimethicone | 5.5-5.0 |
| 144 | Lactic acid | 0.02 to 0.25 wt.-% | Bis-cetearyl amodimethicone | 5.5-5.0 |
| 145 | 1-hydroxyethane-1,1-diphosphonic acid | 0.0001 to 5 wt.-% | Bis-cetearyl amodimethicone | 7.0-6.5 |
| 146 | 1-Hydroxyethane-1,1-diphosphonic acid | 0.001 to 2.5 wt.-% | Bis-cetearyl amodimethicone | 7.0-6.5 |
| 147 | 1-Hydroxyethane-1,1-diphosphonic acid | 0.01 to 1 wt.-% | Bis-cetearyl amodimethicone | 7.0-6.5 |
| 148 | 1-Hydroxyethane-1,1-diphosphonic acid | 0.02 to 0.25 wt.-% | Bis-cetearyl amodimethicone | 7.0-6.5 |
| 149 | 1-Hydroxyethane-1,1-diphosphonic acid | 0.0001 to5 wt.-%. | Bis-cetearyl amodimethicone | 6.5-6.0 |
| 150 | 1-Hydroxyethane-1,1-diphosphonic acid | 0.001 to 2.5 wt.-% | Bis-cetearyl amodimethicone | 6.5-6.0 |
| 151 | 1-Hydroxyethane-1,1-diphosphonic acid | 0.01 to 1 wt.-% | Bis-cetearyl amodimethicone | 6.5-6.0 |
| 152 | 1-Hydroxyethane-1,1-diphosphonic acid | 0.02 to 0.25 wt.-% | Bis-cetearyl amodimethicone | 6.5-6.0 |
| 153 | 1-Hydroxyethane-1,1-diphosphonic acid | 0.0001 to 5 wt.-%. | Bis-cetearyl amodimethicone | 6.0-5.5 |

-continued

| No. | a) Inorganic/organic acid | b) Direct dye | c) Compound(s) of formula (I) | pH of agent |
|---|---|---|---|---|
| 154 | 1-Hydroxyethane-1,1-diphosphonic acid | 0.001 to 2.5 wt.-%. | Bis-cetearyl amodimethicone | 6.0-5.5 |
| 155 | 1-Hydroxyethane-1,1-diphosphonic acid | 0.01 to 1 wt.-% | Bis-cetearyl amodimethicone | 6.0-5.5 |
| 156 | 1-hydroxyethane-1,1-diphosphonic acid | 0.02 to 0.25 wt.-% | Bis-cetearyl amodimethicone | 6.0-5.5 |
| 157 | 1-hydroxyethane-1,1-diphosphonic acid | 0.0001 to 5 wt.-% | Bis-cetearyl amodimethicone | 5.5-5.0 |
| 158 | 1-hydroxyethane-1,1-diphosphonic acid | 0.001 to 2.5 wt.-% | Bis-cetearyl amodimethicone | 5.5-5.0 |
| 159 | 1-hydroxyethane-1,1-diphosphonic acid | 0.01 to 1 wt.-% | Bis-cetearyl amodimethicone | 5.5-5.0 |
| 160 | 1-hydroxyethane-1,1-diphosphonic acid | 0.02 to 0.25 wt.-% | Bis-cetearyl amodimethicone | 5.5-5.0 |

It has been found that adding an organic solvent further improves the luster result. 2-Butoxyethanol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,3-propanediol, glycerin, 1-methoxy-2-propanol, 1-ethoxy-2-propanediol, 1,4-butanediol, 1,3-butanediol, 1,2-hexanediol, benzyl alcohol, phenoxyethanol, 2-phenylethyl alcohol, methoxybutanol, n-butylene glycol, ethylene carbonate, and propylene carbonate may be used as solvent.

Preferred solvents are solvents which contain at least one hydroxy group, for example ethanol, isopropanol, n-propanol, 1,3-propanediol, glycerin, 1-methoxy-2-propanol, 1-ethoxy-2-propanediol, 1,4-butanediol, 1,3-butanediol, 1,2-hexanediol, benzyl alcohol, phenoxyethanol, 2-phenylethyl alcohol, methoxybutanol, and n-butylene glycol.

Particularly preferred are solvents which contain at least two hydroxy groups, for example 1,3-propanediol, glycerin, 1-ethoxy-2-propanediol, 1,4-butanediol, 1,3-butanediol, 1,2-hexanediol, and n-butylene glycol.

The solvents may be contained in the agent according to the invention in a total quantity of 0.1 to 15 wt.-%, preferably 1 to 10 wt.-%, more preferably 1.5 to 8 wt.-%, particular preferably 2 to 6 wt.-%, based on the total weight of the agent.

In another embodiment, an agent according to the invention is characterized in that it contains one or more solvents from the group 2-butoxyethanol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,3-propanediol, glycerin, 1-methoxy-2-propanol, 1-ethoxy-2-propanediol, 1,4-butanediol, 1,3-butanediol, 1,2-hexanediol, benzyl alcohol, phenoxyethanol, 2-phenylethyl alcohol, methoxybutanol, n-butylene glycol, ethylene carbonate, and propylene carbonate in a total quantity of 0.1 to 15 wt.-%, preferably 1 to 10 wt.-%, more preferably 1.5 to 8 wt.-%, and particularly preferably 2 to 6 wt.-%, based on the total weight of the agent.

Moreover, in the studies leading to this invention it has been found that it is possible to increase the luster result even further by adding one or more polyethylene glycols and/or polypropylene glycols. In another preferred embodiment, the agents according to the invention therefore additionally contain at least one polyethylene glycol and/or poylpropylene glycol in a total quantity of 0.1 to 15 wt.-%, preferably 1 to 10 wt.-%, more preferably 1.5 to 8 wt.-%, and particularly preferably 2 to 6 wt.-%, based on the total weight of the agent.

In another preferred embodiment, an agent according to the invention is characterized in that it contains one or more compounds of formula (II)

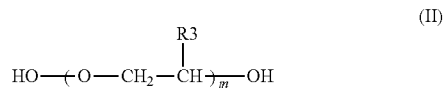

where
R3 stands for a hydrogen atom or a methyl group and
m stands for a number from 2 to 1000,
in a total weight of 0.1 to 15 wt.-%, preferably 1 to 10 wt.-%, more preferably 1.5 to 8 wt.-%, and particularly preferably 2 to 6 wt.-%, based on the total weight of the agent.

The radical R3 may stand for a hydrogen atom or a methyl group. R3 preferably stands for a hydrogen atom.

m stands for a number from 2 to 100. m preferably stands for a number from 10 to 600, particularly preferably for a number from 40 to 500.

Even if the agents according to the invention preferably are set to a neutral to acidic pH, they may, in principle, still contain alkaline reacting compounds such as ammonia or aliphatic alkanolamines, which in the case of the present invention may act as penetration agents and thus allow penetration of the active species into the hair. For increasing the desired pH values, the quantities of the acids used according to the invention may then be correspondingly increased.

In another embodiment, the agent according to the invention is therefore characterized in that it contains 0.01 to 15 wt.-%, preferably 0.1 to 10 wt.-%, particularly preferably 1 to 8 wt.-%, and in particular preferably 3 to 7 wt.-%, based on the total weight of the agent, of a compound selected from ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

If the agents according to the invention are used for the oxidative coloring and/or lightening of hair, in addition to the inorganic/organic acids, the direct dye, and the compound(s) of formula (I), the agents may contain at least one oxidation dye precursor of the developer and/or coupler type as a further component.

According to the invention, agents are preferred which contain the developer and/or coupler components in each case in a weight fraction of 0.001 to 10 wt.-%, preferably 0.01 to 8 wt.-%, particularly preferably 0.1 to 5 wt.-%, and in particular preferably 0.5 to 3 wt.-%, based on the total weight of the agent.

In another preferred embodiment, the agent according to the invention is therefore characterized in that it contains an oxidation dye precursor of the developer and/or coupler type in a weight fraction of 0.001 to 10 wt.-%, preferably 0.01 to 8 wt.-%, particularly preferably 0.1 to 5 wt.-%, and in particular preferably 0.5 to 3 wt.-%, based on the total weight of the agent.

In one preferred embodiment of the first subject matter of the invention, the agent contains as oxidation dye precursor at least one developer component and optionally at least one coupler component. The developer components may form the actual dyes among one another, but preferably with coupler components. The coloring agents according to the invention therefore preferably contain at least one oxidation dye precursor of the developer type and at least one oxidation dye precursor of the coupler type. The developer components and coupler components are usually used in the free form. For substances having amino groups, however, it may be preferred to use the developer components and coupler components in the form of the salt, in particular in the form of the hydrochlorides and hydrobromides or the sulfates.

Developer components and coupler components are generally used in approximately molar quantities with respect to one another. When the molar use has also proven to be practical, a certain excess of individual oxidation dye precursors is not disadvantageous, so that developer components and coupler components may be contained in a molar ratio of 3:1 to 1:3, in particular 2:1 to 1:1.

Suitable oxidation dye precursors of the developer type are p-phenylenediamine and its derivatives. Preferred p-phenylenediamines are selected from one or more compounds of the group comprising p-phenylenediamine, p-toluylenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine, and N-(4-amino-3-methylphenyl)-N-[3-(1H-imidazol-1-yl)propyl]amine and their physiologically acceptable salts.

It may also be preferred according to the invention to use compounds containing at least two aromatic nuclei that are substituted with amino and/or hydroxyl groups as the developer component. Preferred two-nucleus developer components are selected from N,N'-bis-(2-hydroxyethyl)-N,N'-bis-(4'-aminophenyl)-1,3-diaminopropan-2-ol, N,N'-bis-(4-aminophenyl)-1,4-diazacycloheptane, and bis-(2-hydroxy-5-aminophenyl)methane and their physiologically acceptable salts.

Furthermore, it may be preferred according to the invention to use a p-aminophenol derivative or one of its physiologically acceptable salts as the developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, and 4-amino-2-(diethylaminomethyl)phenol and their physiologically acceptable salts.

Moreover, the developer component may be selected from o-aminophenol and its derivatives, preferably from 2-amino-4-methylphenol, 2-amino-5-methylphenol, 2-amino-4-chlorophenol, and/or their physiologically acceptable salts.

In addition, the developer component may be selected from heterocyclic developer components such as pyrimidine derivatives, pyrazole derivatives, pyrazolopyrimidine derivatives, or their physiologically acceptable salts. Preferred pyrimidine derivatives are the compounds 2,4,5,6-tetraaminopyrimidine, 4-hydroxy-2,5,6-triaminopyrimidine, and their physiologically acceptable salts. A preferred pyrazole derivative is 4,5-diamino-1-(2-hydroxyethyl)pyrazole and its physiologically acceptable salts. In particular, pyrazolo[1,5-α]pyrimidines are preferred as pyrazolopyrimidines.

Preferred oxidation dye precursors of the developer type are selected from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of these compounds.

Particularly preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and their physiologically acceptable salts.

Another preferred embodiment of the present invention is characterized in that the agent according to the invention also contains, in addition to at least one developer component, at least one coupler component as oxidation dye precursor. m-Phenylenediamine derivatives, naphthols, resorcinol and resorcinol derivatives, pyrazolones, and m-aminophenol derivatives are generally used as coupler components.

According to the invention, preferred coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)

propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-yl-phenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or the physiologically acceptable salts of the above-mentioned compounds.

According to the invention, particularly preferred coupler components are resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene, and 1-naphthol and any of their physiologically acceptable salts.

Oxidation dye precursors of the developer type and of the coupler type are particularly preferably used in certain combinations. However, even further dye precursors may be combined with the oxidation dye precursors and/or their physiologically acceptable salts, mentioned as a combination: p-toluylenediamine/resorcinol; p-toluylenediamine/2-methylresorcinol; p-toluylenediamine/5-amino-2-methylphenol; p-toluylenediamine/3-aminophenol; p-toluylenediamine/2-(2,4-diaminophenoxy)ethanol; p-toluylenediamine/1,3-bis(2,4-diaminophenoxy)propane; p-toluylenediamine/1-methoxy-2-amino-4-(2-hydroxyethylamino)benzene; p-toluylenediamine/2-amino-3-hydroxypyridine; p-toluylenediamine/1-naphthol; 2-(2-hydroxyethyl)-p-phenylenediamine/resorcinol; 2-(2-hydroxyethyl)-p-phenylenediamine/2-methylresorcinol; 2-(2-hydroxyethyl)-p-phenylenediamine/5-amino-2-methylphenol; 2-(2-hydroxyethyl)-p-phenylenediamine/3-aminophenol; 2-(2-hydroxyethyl)-p-phenylenediamine/2-(2,4-diaminophenoxy)ethanol; 2-(2-hydroxyethyl)-p-phenylenediamine/1,3-bis-(2,4-diaminophenoxy)propane; 2-(2-hydroxyethyl)-p-phenylenediamine/1-methoxy-2-amino-4-(2-hydroxyethylamino)benzene; 2-(2-hydroxyethyl)-p-phenylenediamine/2-amino-3-hydroxypyridine; 2-(2-hydroxyethyl)-p-phenylenediamine/1-naphthol; 2-methoxymethyl-p-phenylenediamine/resorcinol; 2-methoxymethyl-p-phenylenediamine/2-methylresorcinol; 2-methoxymethyl-p-phenylenediamine/5-amino-2-methylphenol; 2-methoxymethyl-p-phenylenediamine/3-aminophenol; 2-methoxymethyl-p-phenylenediamine/2-(2,4-diaminophenoxy)ethanol; 2-methoxymethyl-p-phenylenediamine/1,3-bis(2,4-diaminophenoxy)propane; 2-methoxymethyl-p-phenylenediamine/1-methoxy-2-amino-4-(2-hydroxyethylamino)benzene; 2-methoxymethyl-p-phenylenediamine/2-amino-3-hydroxypyridine; 2-methoxymethyl-p-phenylenediamine/1-naphthol; N-(4-amino-3-methylphenyl)-N-[3-(1H-imidazol-1-yl)propyl]amine/resorcinol; N-(4-amino-3-methylphenyl)-N-[3-(1H-imidazol-1-yl)propyl]amine/2-methylresorcinol; N-(4-amino-3-methylphenyl)-N-[3-(1H-imidazol-1-yl)propyl]amine/5-amino-2-methylphenol; N-(4-amino-3-methylphenyl)-N-[3-(1H-imidazol-1-yl)propyl]amine/3-aminophenol; N-(4-amino-3-methylphenyl)-N-[3-(1H-imidazol-1-yl)propyl]amine/2-(2,4-diaminophenoxy)ethanol; N-(4-amino-3-methylphenyl)-N-[3-(1H-imidazol-1-yl)propyl]amine/1,3-bis(2,4-diaminophenoxy)propane; N-(4-amino-3-methylphenyl)-N-[3-(1H-imidazol-1-yl)propyl]amine/1-methoxy-2-amino-4-(2-hydroxyethylamino)benzene; N-(4-amino-3-methylphenyl)-N-[3-(1H-imidazol-1-yl)propyl]amine/2-amino-3-hydroxypyridine; N-(4-amino-3-methylphenyl)-N-[3-(1H-imidazol-1-yl)propyl]amine/1-naphthol; 4,5-diamino-1-(2-hydroxyethyl)pyrazole/resorcinol; 4,5-diamino-1-(2-hydroxyethyl)pyrazole/2-methylresorcinol; 4,5-diamino-1-(2-hydroxyethyl)pyrazole/5-amino-2-methylphenol; 4,5-diamino-1-(2-hydroxyethyl)pyrazole/3-aminophenol; 4,5-diamino-1-(2-hydroxyethyl)pyrazol/e2-(2,4-diaminophenoxy)ethanol; 4,5-diamino-1-(2-hydroxyethyl)pyrazole/1,3-bis(2,4-diaminophenoxy)propane; 4,5-diamino-1-(2-hydroxyethyl)pyrazole/1-methoxy-2-amino-4-(2-hydroxyethylamino)benzene; 4,5-diamino-1-(2-hydroxyethyl)pyrazole/2-amino-3-hydroxypyridine; 4,5-diamino-1-(2-hydroxyethyl)pyrazol e/1-naphthol.

In one preferred embodiment, however, the agents according to the invention are free of oxidation dye precursors.

In another embodiment of the present invention, the agents according to the invention additionally contain at least one precursor of a natural analog dye. Indoles and indolines which have at least one hydroxy or amino group, preferably as a substituent on the six-membered ring, are preferably used as precursors of natural analog dyes. Particularly preferred derivatives of indoline are 5,6-dihydroxyindoline and 2,3-dioxoindoline (isatin) and their physiologically acceptable salts. A particularly preferred derivative of indole is 5,6-dihydroxyindole and its physiologically acceptable salts. The agents according to the invention contain the indole or indoline derivatives preferably in a weight fraction of 0.05 to 10 wt.-%, preferably 0.2 to 5 wt.-%, in each case based on the total weight of the agent.

In the case of oxidative colorings, the development of the color may in principle take place by means of atmospheric oxygen. However, a chemical oxidizing agent is preferably used, particularly when, in addition to the coloring, a lightening effect on human hair is desired.

To prevent a premature, undesirable reaction of the oxidation dye precursors due to the oxidizing agent, oxidation dye precursors and oxidizing agents themselves are advantageously packaged separately, and brought into contact only immediately before use.

When the agent according to the invention is to be used as an oxidative dye, it is preferably prepared immediately before use by mixing at least two preparations, wherein the at least two preparations are provided in at least two separately packaged containers, and wherein one container contains a coloring and/or lightening agent (A) according to the first subject matter of the invention, and another container contains an oxidizing agent preparation (B) which contains at least one oxidizing agent.

Hydrogen peroxide as well as its solid addition products with organic and inorganic compounds may be used as oxidizing agent. In particular the addition products with urea, melamine, polyvinylpyrrolidinone, and sodium borate are suitable according to the invention as solid addition products. Hydrogen peroxide and/or one of its solid addition products with organic or inorganic compounds is/are particularly preferred as oxidizing agent.

Hydrogen peroxide is particularly preferably used as oxidizing agent. The weight fraction of hydrogen peroxide in the ready-to-apply agent is preferably 0.5 to 12 wt.-%, preferably 2 to 10 wt.-%, and particularly preferably 3 to 6 wt.-% (calculated as 100% $H_2O_2$), in each case based on the total weight of the agent.

A further preferred embodiment of the first subject matter of the invention, therefore, is a ready-to-apply agent, which is characterized in that as oxidizing agent it additionally contains hydrogen peroxide and/or one of the solid addition products thereof with organic or inorganic compounds in a weight fraction of 0.5 to 12 wt.-%, preferably 2 to 10 wt.-%, and particularly preferably 3 to 6 wt.-% (calculated as 100% $H_2O_2$), based on the total weight of the agent.

In one particular embodiment of the invention, just before use, the ready-to-apply agent may be prepared from a color change preparation and an oxidizing agent preparation.

Such oxidizing agent preparations are preferably aqueous oxidizing agent preparations. Preferred preparations are characterized in that the oxidizing agent preparation contains 40 to 95 wt.-%, preferably 50 to 90 wt.-%, particularly preferably 55 to 80 wt.-% water, based on the weight of the oxidizing agent preparation.

However, according to the invention the color change agent as an oxidation coloring agent may also be applied to the hair together with a catalyst which activates the oxidation of the dye precursors, for example by means of atmospheric oxygen. Examples of such catalysts are certain enzymes, iodides, quinones, or metal ions.

Furthermore, it has proven to be advantageous when the agents, in particular the oxidizing agent preparations, contain at least one stabilizer or complexing agent. Examples of chelate complexing agents that are preferred within the scope of the present invention are polycarboxylic acids that are different from acid a), nitrogen-containing mono- or polycarboxylic acids, in particular ethylenediamine tetraacetic acid (EDTA), ethylenediamine disuccinic acid (EDDS), and nitrilotriacetic acid (NTA), geminal diphosphonic acids, in particular 1-hydroxyethane-1,1-diphosphonic acid (HEDP), aminophosphonic acids such as ethylenediaminetetra(methylenephosphonic acid) (EDTMP), and diethylenetriamine penta(methylenephosphonic acid) (DTPMP), phosphonopolycarboxylic acids such as 2-phosphonobutane-1,2,4-tricarboxylic acid, and cyclodextrins, alkali stannates (sodium stannate), alkali pyrophosphates (tetrasodium pyrophosphate, disodium pyrophosphate), alkali phosphates (sodium phosphate), and phosphoric acid. According to the invention, the agents preferably contain 0.01 to 3 wt.-%, preferably 0.05 to 1 wt.-%, of complexing agent, in each case based on the total weight of the agent according to the invention.

For intense lightening of very dark hair, using solely hydrogen peroxide or its addition products with organic or inorganic compounds is often not sufficient. In these cases, a combination of hydrogen peroxide and lightening agents is generally used, which results in increased lightening power of the agent. Bleach boosters are preferred lightening agents. These include peroxo salts, silicon dioxide compounds, and in particular cationized heterocycles.

The bleach booster is preferably selected from ammonium persulfate, alkali metal persulfates, ammonium peroxomonosulfate, alkali metal hydrogen peroxomonosulfates, alkali metal peroxodiphosphates, and alkaline earth metal peroxides. Particularly preferred bleach boosters are ammonium peroxodisulfate, potassium peroxodisulfate, sodium peroxodisulfate, potassium hydrogen peroxomonosulfate, potassium peroxodiphosphate, magnesium peroxide, and barium peroxide. Agents which contain as bleach booster at least one inorganic salt selected from peroxodisulfates are particularly preferred according to the invention. In addition, in the studies for the present invention, it has been found to be particularly preferred when the agents according to the invention contain at least two different peroxodisulfates. Preferred peroxodisulfate salts are combinations of ammonium peroxodisulfate and potassium peroxodisulfate and/or sodium peroxodisulfate.

Persulfate salts or peroxodisulfate salts are generally used in the form of a powder, which optionally is dust-free.

The lightening agents are contained in the agent preferably in a weight fraction of 0.1 to 25 wt.-%, in particular in a quantity of 0.5 to 15 wt.-%, based on the total weight of the ready-to-apply agent.

The statements concerning the agents according to the invention similarly apply with regard to further optional active substances and ingredients of the oxidizing agent preparation.

The agents which are usable according to the invention are preferably formulated as flowable preparations. These include in particular emulsions, suspensions, and gels, particularly preferably emulsions. The flowable preparations preferably additionally contain an emulsifier or a surfactant as surface-active substance, wherein surface-active substances are referred to as surfactants or as emulsifiers, depending on the field of application, and are selected from anionic, cationic, amphoteric, zwitterionic, and nonionic surfactants.

All anionic surface-active substances that are suitable for use on the human body are suited as anionic surfactants in preparations according to the invention. These substances are characterized by a water-solubilizing anionic group such as a carboxylate, sulfate, sulfonate, or phosphate group, and a lipophilic alkyl group containing approximately 8 to 30 C atoms, preferably 8 to 24 C atoms. Glycol ether or polyglycol ether groups, ester, ether, and amide groups, and hydroxyl groups may be additionally contained in the molecule. Preferred anionic surfactants are soaps, alkyl sulfates, alkyl ether sulfates, and ether carboxylic acids containing 8 to 22 C atoms in the alkyl group and up to 12 glycol ether groups in the molecule.

Surface-active compounds bearing at least one quaternary ammonium group and at least one carboxylate, sulfonate, or sulfate group in the molecule are referred to as zwitterionic surfactants. Particularly suitable zwitterionic surfactants are the so-called betaines, such as N-alkyl-N,N-dimethylammonium glycinates, N-acylaminopropyl-N,N-dimethylammonium glycinates, and 2-alkyl-3-carboxymethyl-3-hydroxyethyl imidazolines, and cocacylaminoethylhydroxyethylcarboxymethyl glycinate. One preferred zwitterionic surfactant is the fatty acid amide derivative known under the INCI name cocamidopropyl betaine. In another embodiment of the present invention, the agent further contains at least one amphoteric surfactant Amphoteric surfactants are understood to mean surface-active compounds which, besides a $C_8$-$C_{24}$ alkyl or acyl group in the molecule, also contain at least one free amino group and at least one COOH or $SO_3H$ group, and are capable of forming internal salts. Examples of suitable amphoteric surfactants are N-alkyl glycines, N-alkylpropionic acids, N-alkylaminobutryic acids, N-alkyliminodipropionic acids, N-hydroxyethyl-N-alkylamidopropyl glycines, N-alkyltaurines, N-alkylsarcosines, 2-alkylaminopropionic acids, and alkylaminoacetic acids. Particularly preferred amphoteric surfactants are marketed under the INCI name disodium cocoamphodipropionate with the trade names Miranol C2M SF conc. (Rhodia), Amphoterge K-2 (Lonza), and Monateric CEM-38 (Unichema), and under the name disodium cocoamphodiacetate with the trade names Dehyton (Cognis), Miranol C2M (Rhodia), and Ampholak XCO 30 (Akzo Nobel). In addition, it has proven to be advantageous when the coloring or lightening agents according to the invention contain nonionogenic surface-active substances. Nonionic surfactants contain, for example, a polyol group, a polyalkylene glycol ether group, or a combination of a polyol group and a polyglycol ether group as a hydrophilic group.

Alkylpolyglycosides, in particular $C_8$-$C_{22}$ alkyl mono- and oligoglycosides and their ethoxylated analogs, are preferably suited as nonionic surfactants. The alkylene oxide addition products with saturated linear fatty alcohols and fatty acids, in each case containing 2 to 30 moles ethylene oxide per mole fatty alcohol or fatty acid, have proven suitable as further preferred nonionic surfactants. Saturated or unsaturated $C_{10}$-$C_{22}$ fatty alcohols, in each case containing 2 to 12 moles ethylene oxide per mole fatty alcohol (Laureth-2 or Ceteareth-20, for example), are particularly preferred according to the invention. Preparations with excellent properties are likewise obtained when they contain fatty acid esters of ethoxylated glycerin as nonionic surfactants. The anionic, nonionic, amphoteric, or zwitterionic surfactants are used in total quantities of 0.1 to 45 wt.-%, preferably 1 to 30 wt.-%, and very particularly preferably 1 to 15 wt.-%, based on the total quantity of the ready-to-apply agent.

Cationic surfactants of the quaternary ammonium compound, esterquat, and alkylamidoamine types are likewise preferred according to the invention. Preferred quaternary ammonium compounds are ammonium halides such as alkyltrimethylammonium chlorides, dialkyldimethylammonium chlorides, and trialkylmethylammonium chlorides, and the imidazolium compounds known under the INCI names Quaternium-27 and Quaternium-83. The long alkyl chains of the above-mentioned surfactants preferably have 10 to 18 carbon atoms. Further cationic surfactants which are usable according to the invention are quaternized protein hydrolysates. Alkylamidoamines are customarily produced by amidation of natural or synthetic fatty acids and fatty acid fractions with dialkylaminoamines. Tego Amid® S18 (stearamidopropyl dimethylamine) represents a compound from this substance group which is suitable according to the invention. Esterquats are substances which contain at least one ester function and at least one quaternary ammonium group as the structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are marketed under the trademarks Stepantex, Dehyquart, and Armocare. The cationic surfactants are preferably contained in the agents used according to the invention in quantities of 0.05 to 10 wt.-%, based on the overall agent. Quantities of 0.1 to 5 wt.-% are particularly preferred.

At least one amphoteric or zwitterionic surfactant is particularly preferably used in the agents according to the invention.

In another embodiment of the first subject matter of the invention, an agent according to the invention is characterized in that it additionally contains at least one amphoteric and/or zwitterionic surfactant.

Accordingly, agents are particularly preferred which contain
a) at least one inorganic and/or organic acid
b) at least one direct dye and
c) at least one compound of formula (I) described above and
d) at least one amphoteric and/or zwitterionic surfactant.

In addition, the agents according to the invention may contain further active substances, auxiliary substances, and additives, for example associative polymers having a fatty alkyl chain, cationic polymers, nonionic polymers (vinyl pyrrolidinone/vinyl acrylate copolymers, polyvinylpyrrolidinone, vinyl pyrrolidinone/vinyl acetate copolymers, polyethylene glycols, and polysiloxanes); zwitterionic and amphoteric polymers (acrylamidopropyl trimethylammonium chloride/acrylate copolymers and octylacrylamide/methylmethacrylate/tert-butylaminoethyl methacrylate/2-hydroxypropyl methacrylate copolymers); anionic polymers (polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers, and acrylic acid/ethyl acrylate/N-tert-butylacrylamide terpolymers); thickeners (agar agar, guar gum, alginates, xanthan gum, gum arabic, karaya gum, locust bean gum, flaxseed gum, dextrans, cellulose derivatives such as methylcellulose, hydroxyalkylcellulose, and carboxymethylcellulose, starch fractions and derivatives such as amylose, amylopectin, and dextrins, clays such as bentonite or fully synthetic hydrocolloids such as polyvinyl alcohol); structurizers (glucose, maleic acid, and lactic acid), hair conditioning compounds (phospholipids, soy lecithin, egg lecithin, cephalins, and silicone oils); additional protein hydrolysates of plant or animal origin (elastin, collagen, keratin, milk protein, soy protein, and wheat protein hydrolysates, condensation products thereof with fatty acids and quaternized protein hydrolysates); fragrance oils, dimethyl isosorbide, and cyclodextrins; fiber structure-improving active substances (mono-, di-, and oligosaccharides, glucose, maleic acid, and lactic acid); defoamers such as silicones (dimethicone); dyes for coloring the agent; anti-dandruff active substances (piroctone olamines, zinc omadines, and climbazole); light protection agents (derivatized benzophenones, cinnamic acid derivatives, and triazines); active substances (panthenol, pantothenic acid, pantolactone, allantoin, pyrrolidinone carboxylic acids and their salts, bisabolol, carnitine, caffeine, theobromine, and taurine); vitamins, provitamins, and vitamin precursors, in particular those of groups A, $B_3$, $B_5$, $B_6$, C, E, F, and H; plant extracts (from green tea, oak bark, nettle, witch hazel, hops, chamomile, burdock root, horsetail, hawthorn, lime blossom, almond, aloe vera, spruce needle, horse chestnut, sandalwood, juniper berry, coconut, mango, apricot, lemon, lychee, wheat, kiwi fruit, melon, orange, grapefruit, sage, rosemary, birch, mallow, cuckoo flower, wild thyme, yarrow, thyme, lemon balm, moringa, restharrow, coltsfoot, marsh mallow, meristem, ginseng, and ginger); plant oils (macadamia nut oil, kukui nut oil, palm oil, amaranth seed oil, peach kernel oil, avocado oil, olive oil, coconut oil, rapeseed oil, sesame oil, jojoba oil, soy oil, peanut oil, evening primrose oil, tea tree oil); cholesterol; consistency enhancers (sugar esters, polyol esters, or polyol alkyl ethers); fats and waxes (fatty alcohols, beeswax, montan wax, and paraffins); swelling agents and penetration agents (glycerin, propylene glycol monoethyl ether, carbonates, hydrogen carbonates, guanidines, ureas, and primary, secondary, and tertiary phosphates); opacifiers (latex, styrene/PVP and styrene/acrylamide copolymers); pearlescence agents (ethylene glycol monostearate and PEG-3-distearate); propellants such as propane-butane mixtures, $N_2O$, dimethyl ether, $CO_2$, and air; antioxidants.

Agents containing at least one cationic polymer are likewise preferred for achieving the object of the invention. Accordingly, agents are particularly preferred which contain
a) at least one inorganic and/or organic acid
b) at least one direct dye and
c) at least one compound at least one compound of formula (I) described above and
d) at least one cationic polymer.

In another embodiment of the first subject matter of the invention, an agent according to the invention is characterized in that it contains at least one cationic polymer from the group Polyquaternium-4, Polyquatemium-6, Polyquaternium-7, Polyquaternium-8, Polyquatemium-10, Polyquaternium-11, Polyquaternium-22, Polyquatemium-24, Polyquaternium-32, Polyquatemium-37, Polyquaternium-39, Polyqaternium-44, Polyquaternium-46, Polyquaternium-53, Polyquatemium-55, Polyquaternium-64, Polyquaternium-68, Polyquaternium-69, Polyquaternium-87, and Polyquatemium-91.

The cationic polymer(s) may be contained in the agent according to the invention in a total quantity of 0.01 to 25 wt.-%, preferably 0.1 to 10 wt.-%, in particular 0.5 to 5 wt.-%.

In one very particularly preferred embodiment, the agent according to the invention additionally contains 0.5 to 5 wt.-% Polyquaternium-6. In another preferred embodiment, the agent according to the invention is characterized in that it contains 0.5 to 5 wt.-% Polyquaternium-6.

Furthermore, the agent according to the invention may additionally contain at least one active substance, auxiliary substance, and additive from the group comprising
a) structurizers selected from glucose, maleic acid, and lactic acid,
b) hair conditioning compounds selected from phospholipids, soy lecithin, egg lecithin, cephalins, and silicone oils,
c) protein hydrolysates selected from elastin, collagen, keratin, milk protein, soy protein, and wheat protein hydrolysates, and condensation products thereof with fatty acids and quaternized protein hydrolysates,
d) active substances selected from panthenol, pantothenic acid, pantolactone, allantoin, pyrrolidinone carboxylic acids and their salts, bisabolol, carnitine, caffeine, theophylline, theobromine, and taurine,
e) vitamins, provitamins, and vitamin precursors, and
f) plant extracts.

Those skilled in the art will select these further substances according to the desired properties of the preparations. The preparations contain the further active substances, auxiliary substances, and additives preferably in a weight fraction of 0.01 to 25 wt.-%, in particular 0.05 to 15 wt.-%, based on the total quantity of the ready-to-apply agent.

The agent according to the invention is preferably a one-component agent. However, the agents according to the invention may also be prepared from two or more separately packaged preparations directly before use. This is useful in particular for separating incompatible ingredients to avoid a premature reaction. Separation into multicomponent systems is useful in particular where there is an expectation of or concern for incompatibilities of the ingredients. In such systems, the ready-to-apply agent is prepared by the consumer directly before application by mixing the components. This procedure is particularly preferred in the case of an oxidative dye, in which the oxidation dye precursors are initially present separate from an oxidizing agent preparation which preferably contains hydrogen peroxide.

A further subject matter of the invention, therefore, relates to a multicomponent packaging unit ("kit of parts") for coloring and/or lightening keratinic fibers, the multicomponent packaging unit containing a first separately packaged container (A) which contains at least one agent according to the first subject matter of the invention, and containing at least one second, separately packaged container (B) which contains at least one agent containing hydrogen peroxide.

The agents of the first subject matter of the invention may be used for coloring and/or shading hair, and, if they additionally contain an oxidizing agent, also for lightening hair. In addition to the coloring or shading, the agents according to the invention also produce an intense, long-lasting luster on the hair.

A further subject matter of the present invention, therefore, relates to the cosmetic nontherapeutic use of an agent of the first subject matter of the invention for producing a long-lasting luster on keratinic fibers.

The agents of the first subject matter of the invention may be used in methods for coloring, shading, and/or lightening human hair. If the agents are used as a shading agent, the shading may be carried out directly afterwards, i.e., several hours or one day maximum after coloring has been performed. However, it is likewise conceivable for a period from one to several weeks, preferably 10 to 14 days, to elapse between the coloring and the shading which is carried out using the agent according to the invention.

For the coloring or shading, an agent of the first subject matter of the invention is applied to the hair and left in the hair for a period of 30 seconds to 45 minutes, preferably 1 to 30 minutes, particularly preferably 2 to 15 minutes. The hair is subsequently rinsed with water and/or a standard shampoo. If desired, the hair may subsequently be treated with a further agent and then rinsed once again with water and/or a standard shampoo.

A further subject matter of the present invention, therefore, relates to a method for producing a long-lasting luster on keratinic fibers, in particular human hair, in which an agent of the first subject matter of the invention is applied to the keratinic fibers, left there for 30 seconds to 45 minutes, and subsequently rinsed out with water or a surfactant-containing agent.

The application temperature and exposure temperature of the coloring and/or lightening preparation is room temperature to 45° C. The action of the coloring and/or lightening preparation may optionally be intensified by supplying external heat, using a hood hair dryer, for example. After the exposure time has ended, the remaining coloring and/or lightening agent is washed out of the keratinic fibers by means of a cleaning preparation or water. The process is optionally repeated using a further agent. After the agent is washed out, the keratinic fibers are optionally dried using a towel or a hot air blower. The coloring and/or lightening preparation is usually applied by hand by the user. Personal protective clothing is preferably worn, in particular suitable protective gloves made of plastic or latex for one-time use (disposable gloves), and optionally an apron. However, it is also possible to apply the coloring and/or lightening agent to the keratinic fibers using an application aid.

The statements concerning the agents according to the invention similarly apply with regard to further embodiments of the methods and uses according to the invention.

EXAMPLES

Quantities are understood to be expressed in each case in percent by weight unless noted otherwise.

1.1 Formulations

The following formulations were produced. V1 to V3 are comparative formulations not according to the invention, and E is a formulation according to the invention.

| Description | V1 | V2 | V3 | E |
|---|---|---|---|---|
| Lorol $C_{12}$-$C_{18}$, technical grade | 4.0 | 4.0 | 4.0 | 4.0 |
| Cocamidopropyl betaine | 4.5 | 4.5 | 4.5 | 4.5 |
| Texapon NSO | 4.0 | 4.0 | 4.0 | 4.0 |
| Dehydol LS 2 Deo N | 0.8 | 0.8 | 0.8 | 0.8 |
| Emulgade 1000 NI | 2.4 | 2.4 | 2.4 | 2.4 |
| Methylparaben | 0.4 | 0.4 | 0.4 | 0.4 |
| Propylparaben | 0.19 | 0.19 | 0.19 | 0.19 |
| Polyethylene glycol | 4.0 | 4.0 | 4.0 | 4.0 |
| 1,3-Butanediol | 1.0 | 1.0 | 1.0 | 1.0 |
| Carbomer | 1.0 | 1.0 | 1.0 | 1.0 |
| Polyquaternium-6 | 1.0 | 1.0 | 1.0 | 1.0 |
| HC Yellow 2 | 0.013 | — | — | 0.013 |
| HC Blue 12 | 0.04 | — | — | 0.04 |
| 2-Amino-6-chloro-4-nitrophenol | 0.013 | — | — | 0.013 |
| N,N-bis(2-hydroxyethyl)-2-nitro-p-phenylenediamine | 0.006 | — | — | 0.006 |
| Silsoft AX | — | 1.0 | — | 1.0 |
| 1-Hydroxyethane-1,1-diphosphonic acid | To give pH 6.7 | To give pH 6.7 | — | To give pH 6.7 |
| Monoethanolamine | 0.73 | 0.73 | To give pH 8.7 | 0.73 |
| Distilled water | To make 100% | To make 100% | To make 100% | To make 100% |

Raw materials used:

Lorol $C_{12}$-$C_{18}$, technical grade $C_{12}$-$C_{18}$ fatty alcohols
Texapon NSO Sodium polyoxyethylene lauryl ether sulfate/sodium polyoxyethylene myristyl ether sulfate (27% aqueous solution)
Dehydol LS 2 Deo N Polyoxyethylene (2) dodecyl ether (INCI: Laureth-2)
Emulgade 1000 NI Cetearyl alcohol (80-100%), Ceteareth-20 (10-20%)
Carbomer (Polyacrylic acid)
Silsoft AX (INCI name: bis-cetearyl amodimethicone [Momentive])

1.2. Instrumental Determination of Hair Luster

Hair tresses 4 cm in width and 15 cm in length (Kerling, Natural European Hair 6/0) were precleaned with a 0.3% solution of Texapon (pH 6-7, INCI name: SODIUM LAURETH SULFATE) and dried. These strands were measured in a luster apparatus.

The previously produced formulations V1, V2, V3, and E were each applied to one hair tress (4 g application mixture per g of hair) and allowed to act for 30 min at 32° C. The tresses were subsequently rinsed out with tap water and dried. The dried hair strands were measured a second time in a luster apparatus. The hair tresses were subsequently washed three times with an aqueous shampoo solution and dried. The strands were then measured a third time in the luster apparatus.

The luster apparatus was a luster chamber provided with a light-absorbing lining. The hair strands to be measured were clamped onto a cylinder and positioned in the middle of the luster chamber. As the illumination source, a rod-shaped gas discharge lamp which illuminated the hair strands, clamped onto the cylinder, through a small aperture was situated above the cylinder. The luster curve of each strand was measured using a digital camera and evaluated by image analysis. The luster value of the strands (L) was subsequently calculated according to the Reich and Robbins formula (1):

$$L_{Reich/Robbins} = \frac{S}{D * W^{1/2}}$$

L: luster
S: directed reflection
D: diffuse reflection
W½: half-width of the luster curve
(1) C. Reich and C. C. Robbins, J. Soc. Cosmet. Chem. 44, 221-234 (1993)

The following luster values were obtained. The higher the luster value, the higher the luster.

| Luster value | Hair luster prior to use (initial value) | Hair luster directly after application | h = Hair luster after 3 hair washings |
|---|---|---|---|
| V1 | 0.0114 | 0.0131 | 0.0133 |
| V2 | 0.0128 | 0.0126 | 0.0124 |
| V3 | 0.0120 | 0.0143 | 0.0128 |
| E | 0.0124 | 0.0178 | 0.0151 |

It is clearly shown that the highest luster values could be measured with the hair tresses that had been treated with formulation E, directly after application as well as after three hair washings.

In comparison to comparative formulations V1 to V3, formulation E according to the invention showed the highest luster, directly after application as well as after three hair washings.

1.3. Determination of Hair Luster in Test Salon Experiments

Formulations V1 and E were used on each of three test subjects in the half-side test. For this purpose, formulation V1 was applied to one half of the head, and formulation E was applied to the other half of the head.

After application, the formulations were rinsed off and the hair was dried. The luster result was subsequently visually assessed for each formulation. After three hair washings, the luster result was visually assessed a second time.

The following results were obtained for all three test subjects:

| Hair luster, visually assessed | Hair luster directly after application | Hair luster after 3 hair washings |
|---|---|---|
| V1 | Hair luster present, slightly less intense than for E | No luster |
| E | Hair luster present, slightly more intense than for V1 | Fairly intense luster still noticeable |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for treating keratinic fibers in a cosmetically suitable carrier, comprising:
   a) at least one inorganic and/or organic acid
   b) at least one direct dye and
   c) at least one compound of formula (I)

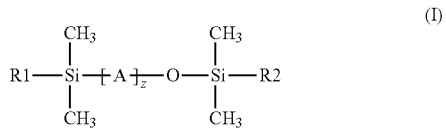

where
A=

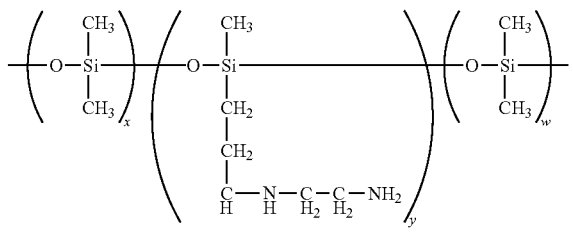

wherein
   i. x and y independently stand for numbers from 1 to 100,
   ii. w stands for a number from 0 to 100,
   iii. z stands for a number from 1 to 100, where, if z≥2, the respective values x, y, and w in a structural element A may be selected in each case independently of preceding structural elements A,
   and a
   iv. R1 and R2 independently stand for a linear or branched, saturated, unsaturated, or multiply unsaturated $C_5$-$C_{20}$ alkyl group, a hydroxy group, a $C_1$-$C_{30}$ alkoxy group, a carboxy-$C_1$-$C_{30}$ alkyl group, or a $C_1$-$C_6$ alkyl-(O—$CH_2$—$CH_2$)$_n$—O— group, wherein n stands for an integer from 1 to 60
   d) comprising 0.1 wt % to 15 wt % of one or more compounds of formula (II)

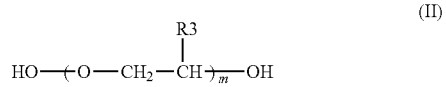

where
R3 stands for a hydrogen atom or a methyl group and m stands for a number from 2 to 1000.

2. The agent according to claim 1, wherein the at least one acid includes an acid selected from the group consisting of from citric acid, tartaric acid, malic acid, lactic acid, 1-hydroxyethane-1,1-diphosphonic acid, 2,6-dipicolinic acid, and benzoic acid.

3. The agent according to claim 1, wherein in that the agent has a pH of 2 to 7 at a temperature of 22° C.

4. The agent according to claim 1, wherein the agent has a pH of 3 to 6.9 at a temperature of 22° C.

5. The agent according to claim 1, wherein the agent has a pH of 4 to 6.8 at a temperature of 22° C.

6. The agent according to claim 1, wherein the one or more direct dye comprise 0.0001 wt % to 5 wt % of the total weight of the agent.

7. The agent according to claim 1, wherein the one or more direct dyes comprise 0.001 wt % to 2.5 wt % of the total weight of the agent.

8. The agent according to claim 1, wherein the one or more direct dyes comprise 0.01 wt % to 1 wt % of the total weight of the agent.

9. The agent according to claim 1, wherein the at least direct dye includes at least one nonionic nitro dye.

10. The agent according to claim 1, wherein the at least one direct dyes includes a combination of direct dyes selected from the group consisting of: HC Blue 12/HC Yellow 2, HC Blue 12/HC Yellow 4, HC Blue 12/HC Yellow 5, HC Blue 12/HC Yellow 6, HC Blue 12/HC Yellow 12, HC Blue 12/HC Orange 1, HC Blue 12/HC Red 1, HC Blue 12/HC Red 3, HC Blue 12/HC Red 7, HC Blue 12/HC Red 10, HC Blue 12/HC Red 11, HC Blue 12/HC Red 13, HC Blue 12/HC Red BN, HC Blue 12/HC Violet 1, HC Blue 12/1,4-diamino-2-nitrobenzene, HC Blue 12/2-amino-4-nitrophenol, HC Blue 12/1,4-bis-(2-hydroxyethyl)amino-2-nitrobenzene, HC Blue 12/3-nitro-4-(2-hydroxyethyl)aminophenol, HC Blue 12/4-[(2-hydroxyethyl)amino]-3-nitro-1-methylbenzene, HC Blue 12/1-amino-4-(2-hydroxyethyl)amino-5-chloro-2-nitrobenzene, HC Blue 12/1-amino-4-(2-hydroxyethyl)amino-5-chloro-2-nitrobenzene, HC Blue 12/4-amino-3-nitrophenol, HC Blue 12/4-[(3-hydroxypropyl)amino]-3-nitrophenol, HC Blue 12/2-amino-6-chloro-4-nitrophenol, HC Blue 12/4-ethylamino-3-nitrobenzoic acid, HC Blue 12/2-chloro-6-ethylamino-4-nitrophenol, HC Yellow 2/HC Yellow 4, HC Yellow 2/HC Yellow 5, HC Yellow 2/HC Yellow 6, HC Yellow 2/HC Yellow 12, HC Yellow 2/HC Orange 1, HC Yellow 2/HC Red 1, HC Yellow 2/HC Red 3, HC Yellow 2/HC Red 7, HC Yellow 2/HC Red 10, HC Yellow 2/HC Red 11, HC Yellow 2/HC Red 13, HC Yellow 2/HC Red BN, HC Yellow 2/HC Violet 1, HC Yellow 2/HC Blue 2, HC Yellow 2/HC Blue 11, HC Yellow 2/HC Blue 12, HC Yellow 2/1,4-diamino-2-nitrobenzene, HC Yellow 2/2-amino-4-nitrophenol, HC Yellow 2/1,4-bis-(2-hydroxyethyl)amino-2-nitrobenzene, HC Yellow 2/3-nitro-4-(2-hydroxyethyl)aminophenol, HC Yellow 2/4-[(2-hydroxyethyl)amino]-3-nitro-1-methylbenzene, HC Yellow 2/1-amino-4-(2-hydroxyethyl)amino-5-chloro-2-nitrobenzene, HC Yellow 2/4-amino-3-nitrophenol, HC Yellow 2/4-[(3-hydroxypropyl)amino]-3-nitrophenol/HC Yellow 2/2-amino-6-chloro-4-nitrophenol, HC Yellow 2/4-ethylamino-3-nitrobenzoic acid, or HC Yellow 2/2-chloro-6-ethylamino-4-nitrophenol, 2-amino-6-chloro-4-nitrophenol/HC Yellow 2, 2-amino-6-chloro-4-nitrophenol/HC Yellow 4, 2-amino-6-chloro-4-nitrophenol/HC Yellow 5, 2-amino-6-chloro-4-nitrophenol/HC Yellow 6, 2-amino-6-chloro-4-nitrophenol/HC Yellow 12, 2-amino-6-chloro-4-nitrophenol/HC Orange 1, 2-amino-6-chloro-4-nitrophenol/HC Red 1, 2-amino-6-chloro-4-nitrophenol/HC Red 3, 2-amino-6-chloro-4-nitrophenol/HC Red 7, 2-amino-6-chloro-4-nitrophenol/HC Red 10, 2-amino-6-chloro-4-nitrophenol/HC Red 11, 2-amino-6-chloro-4-nitrophenol/HC Red 13, 2-amino-6-chloro-4-nitrophenol/HC Red BN, 2-amino-6-chloro-4-nitrophenol/HC Blue 2, 2-amino-6-chloro-4-nitrophenol/HC Blue 11, 2-amino-6-chloro-4-nitrophenol/HC Blue 12, 2-amino-6-chloro-4-nitrophenol/HC Violet 1, 2-amino-6-chloro-4-nitrophenol/1,4-diamino-2-nitrobenzene, 2-amino-6-chloro-4-nitrophenol/2-amino-4-nitrophenol, 2-amino-6-chloro-4-nitrophenol/1,4-bis-(2-hydroxyethyl)amino-2-nitrobenzene, 2-amino-6-chloro-4-nitrophenol/3-nitro-4-(2-hydroxyethyl)aminophenol, 2-amino-6-chloro-4-nitrophenol/4-[(2-hydroxyethyl)amino]-3-nitro-1-methylbenzene, 2-amino-6-chloro-4-nitrophenol/1-amino-4-(2-hydroxyethyl)amino-5-chloro-2-nitrobenzene, 2-amino-6-chloro-4-nitrophenol/4-amino-3-nitrophenol, 2-amino-6-chloro-4-nitrophenol/4-[(3-hydroxypropyl)amino]-3-nitrophenol, 2-amino-6-chloro-4-nitrophenol/4-ethylamino-3-nitrobenzoic acid, and 2-amino-6-chloro-4-nitrophenol/2-chloro-6-ethylamino-4-nitrophenol.

11. The agent according to claim 1, wherein the substituents R1 and R2 independently stand for a linear or branched, saturated, unsaturated, or multiply unsaturated $C_5$-$C_{20}$ alkyl chain.

12. The agent according to claim 1, wherein the substituents R1 and R2 independently stand for a linear or branched, saturated, unsaturated, or multiply unsaturated $C_{14}$-$C_{20}$ alkyl chain.

13. The agent according to claim 1, wherein the substituents R1 and R2 independently are selected from the group consisting of: $H_3C-(CH_2)_{13}-$, $H_3C-(CH_2)_{15}-$, $H_3C-(CH_2)_{17}-$, and $H_3C-(CH_2)_{19}-$.

14. The agent according to claim 1, wherein the compound or compounds of formula (I) comprise 0.005 wt % to 5 wt % of the total weight of the agent.

15. The agent according to claim 1, wherein the compound or compounds of formula (I) comprise 0.1 wt % to 4.5 wt % of the total weight of the agent.

16. The agent according to claim 1, wherein the compound or compounds of formula (I) comprise 1.5 wt % to 2.5 wt % of the total weight of the agent.

17. The agent according to claim 1, wherein the agent characterized further comprises 0.1 wt % to 15 wt % of one or more solvents selected from the group consisting of: 2-butoxyethanol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,3-propanediol, glycerin, 1-methoxy-2-propanol, 1-ethoxy-2-propanediol, 1,4-butanediol, 1,3-butanediol, 1,2-hexanediol, benzyl alcohol, phenoxyethanol, 2-phenylethyl alcohol, methoxybutanol, n-butylene glycol, ethylene carbonate, and propylene carbonate.

18. Method for producing a long-lasting luster on keratinic fibers, in particular human hair, in which an agent according to claim 1 is applied to the keratinic fibers, left there for 30 seconds to 45 minutes, and subsequently rinsed out with water or a surfactant-containing agent.

* * * * *